United States Patent [19]

Boguslaski et al.

[11] 4,404,366
[45] * Sep. 13, 1983

[54] BETA-GALACTOSYL-UMBELLIFERONE-LABELED HAPTEN CONJUGATES

[75] Inventors: Robert C. Boguslaski; John F. Burd; Robert J. Carrico, all of Elkhart, Ind.

[73] Assignee: Miles Laboratories, Inc., Elkhart, Ind.

[*] Notice: The portion of the term of this patent subsequent to Oct. 7, 1997, has been disclaimed.

[21] Appl. No.: 284,137

[22] Filed: Jul. 16, 1981

Related U.S. Application Data

[60] Division of Ser. No. 147,339, May 6, 1980, Pat. No. 4,331,590, which is a division of Ser. No. 87,819, Oct. 23, 1979, Pat. No. 4,279,992, which is a continuation-in-part of Ser. No. 886,094, Mar. 13, 1978, Pat. No. 4,226,978.

[51] Int. Cl.³ .............................................. C07H 15/24
[52] U.S. Cl. .................................... 536/18.1; 424/180; 424/2; 424/7.1; 536/4.1; 536/13.6; 536/13.7; 536/13.9; 536/16.8; 536/5
[58] Field of Search .................... 536/4, 17 R, 5, 6, 7, 536/4.1, 18.1

[56] References Cited
U.S. PATENT DOCUMENTS

| | | | |
|---|---|---|---|
| 4,226,978 | 10/1980 | Boguslaski et al. | 536/4 |
| 4,259,233 | 3/1981 | Carrico et al. | 536/4 |
| 4,279,992 | 7/1981 | Boguslaski et al. | 424/8 |
| 4,292,425 | 9/1981 | Buckler et al. | 536/4 |
| 4,331,590 | 5/1982 | Boguslaski et al. | 536/17 R |

Primary Examiner—Johnnie R. Brown
Attorney, Agent, or Firm—Andrew L. Klawitter

[57] ABSTRACT

An improved specific binding assay method and reagent for determining a ligand in a liquid medium employing, as an enzyme-cleavable substrate label, a residue having the formula:

$$G-D-R$$

wherein G is a glycone, D is a dye indicator moiety, and R is a linking group through which the label residue is covalently bound to a binding component of a conventional binding assay system, such as the ligand, an analog thereof, or a specific binding partner thereof. The monitored characteristic of the label is the release of a detectable product, usually a fluorogen or chromogen, upon enzymatic cleavage of the glycosidic linkage between the glycone and the dye indicator moiety. The assay method may follow a homogeneous or heterogeneous format. The preferred glycone is a β-galactosyl group and the preferred dye indicator moiety is an umbelliferone residue. The improved assay is particularly suited to the determination of haptens, such as drugs, and antigenic proteins and polypeptides, including antibodies, following a homogeneous competitive binding assay format.

11 Claims, 21 Drawing Figures

DRUG IMMUNOASSAY

I. ENZYMATIC REACTION

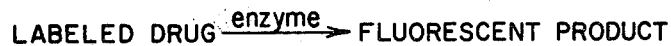
LABELED DRUG $\xrightarrow{\text{enzyme}}$ FLUORESCENT PRODUCT

II. ANTIBODY BINDING REACTION

LABELED DRUG + ANTIBODY $\rightleftarrows$ LABELED DRUG - ANTIBODY COMPLEX $\xrightarrow{\text{enzyme}}$ NO REACTION

III COMPETITIVE BINDING REACTION

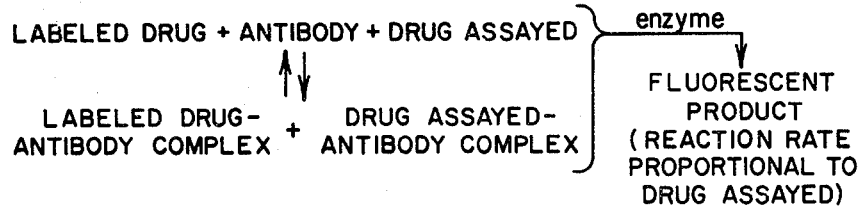
LABELED DRUG + ANTIBODY + DRUG ASSAYED $\updownarrow$ LABELED DRUG-ANTIBODY COMPLEX + DRUG ASSAYED-ANTIBODY COMPLEX $\xrightarrow{\text{enzyme}}$ FLUORESCENT PRODUCT (REACTION RATE PROPORTIONAL TO DRUG ASSAYED)

FIG. 1

INHIBITION OF LABELED CONJUGATE FOR GENTAMICIN ASSAY

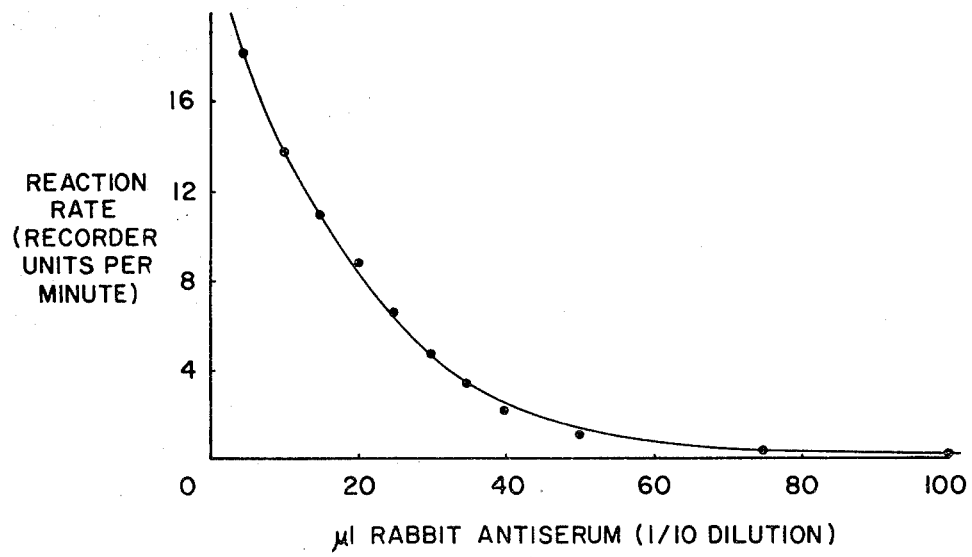

FIG. 2

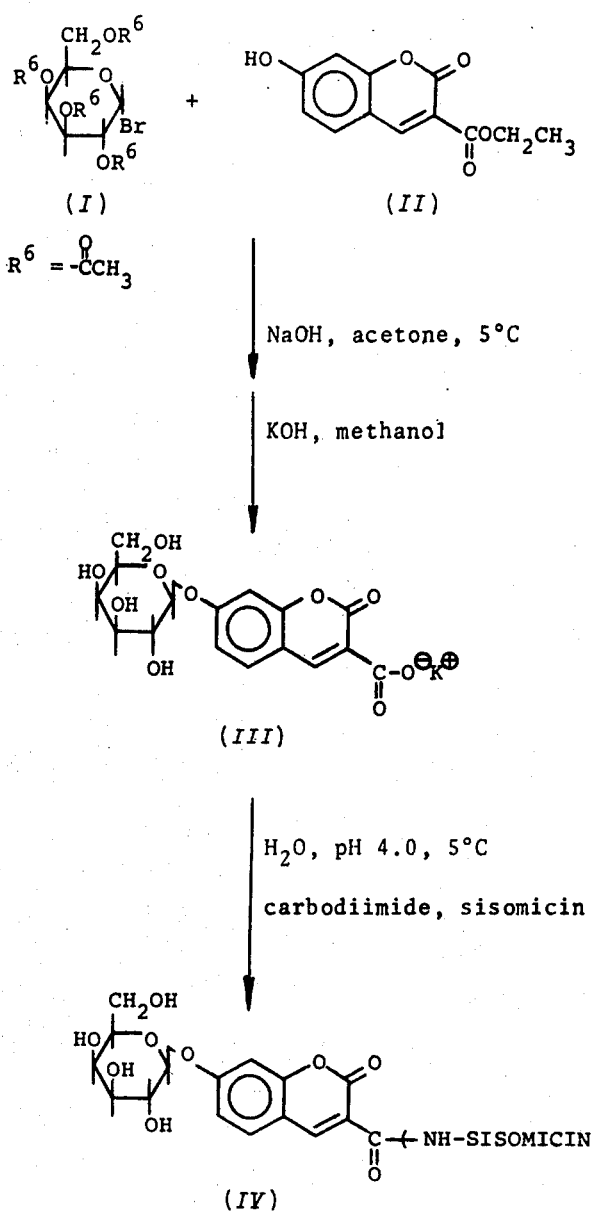
TABLE A

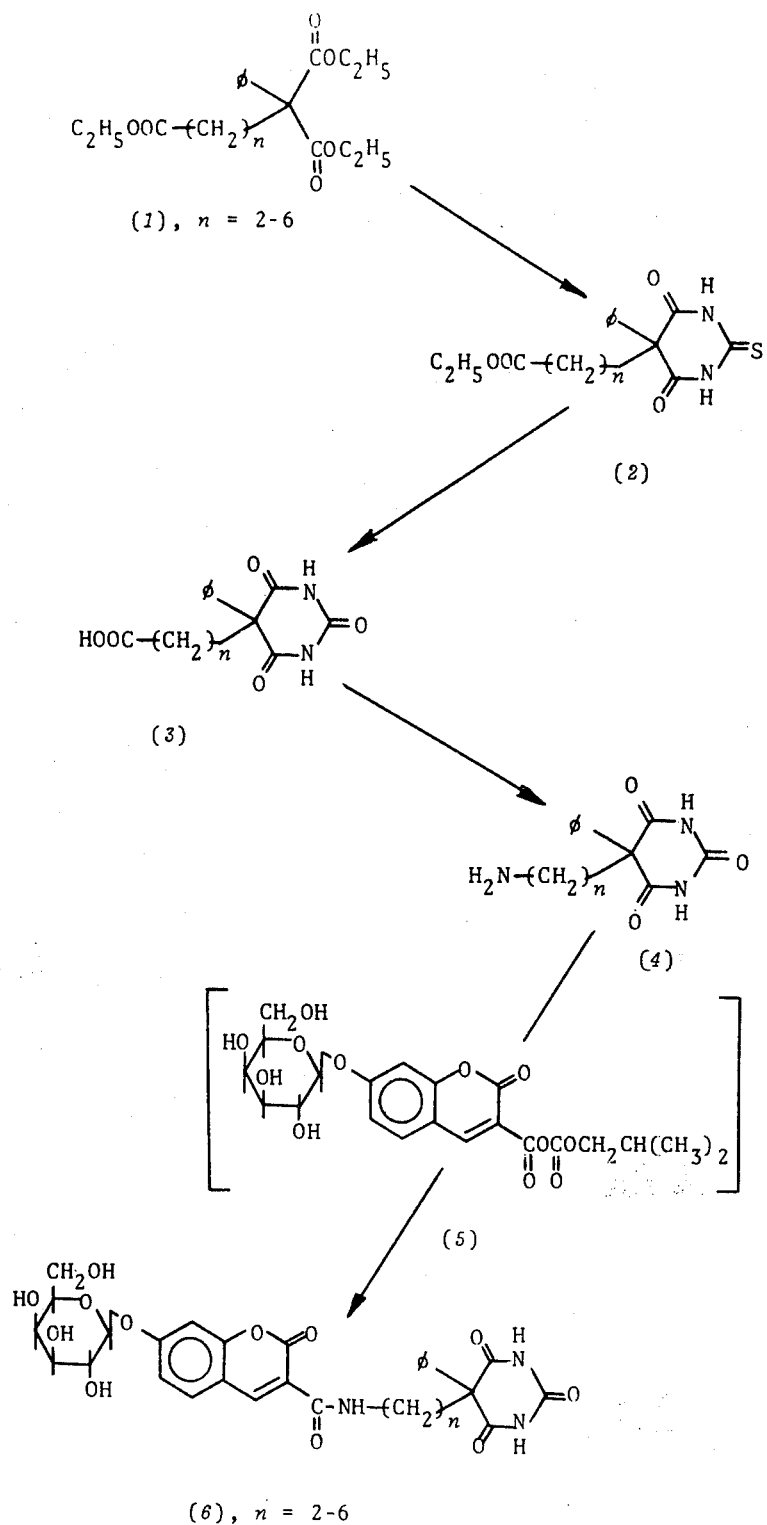
TABLE B

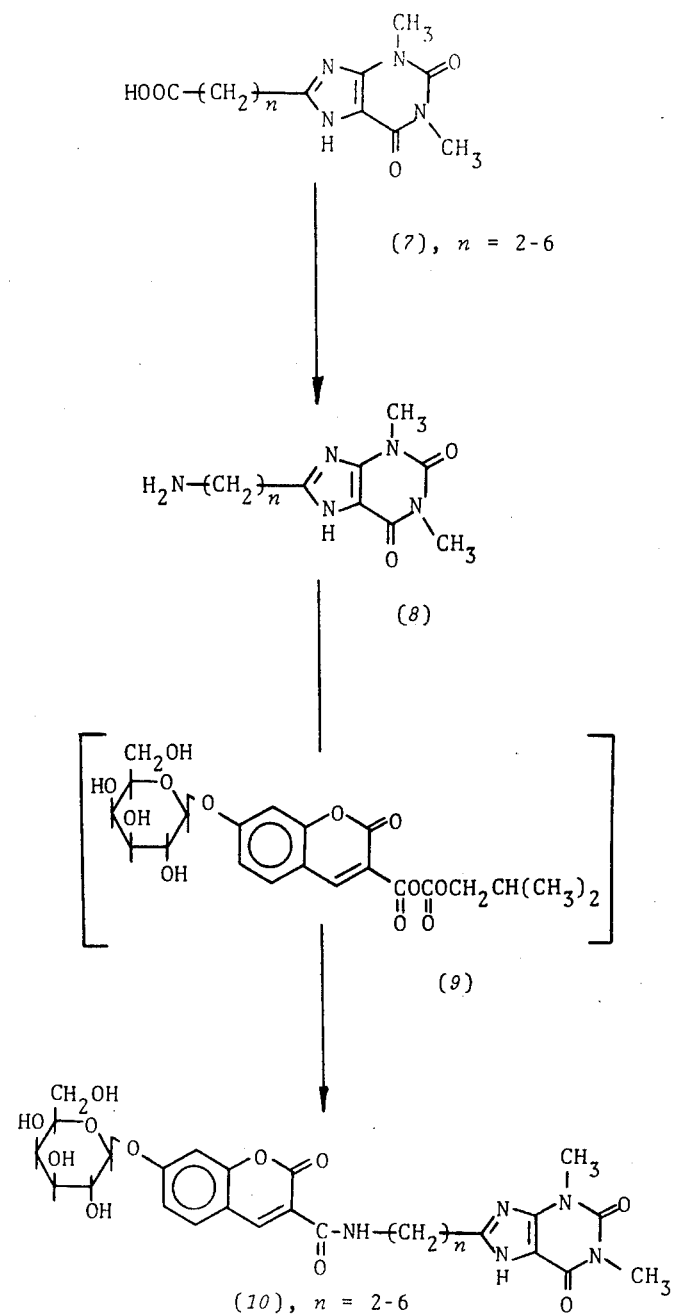
TABLE C

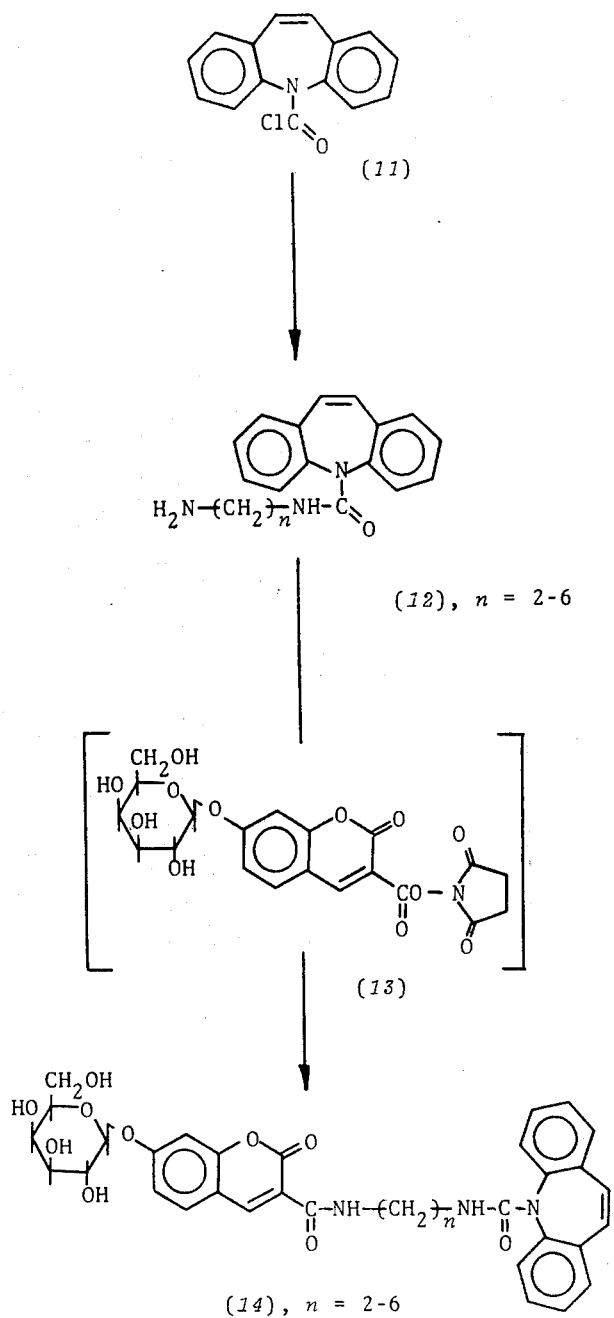
TABLE D

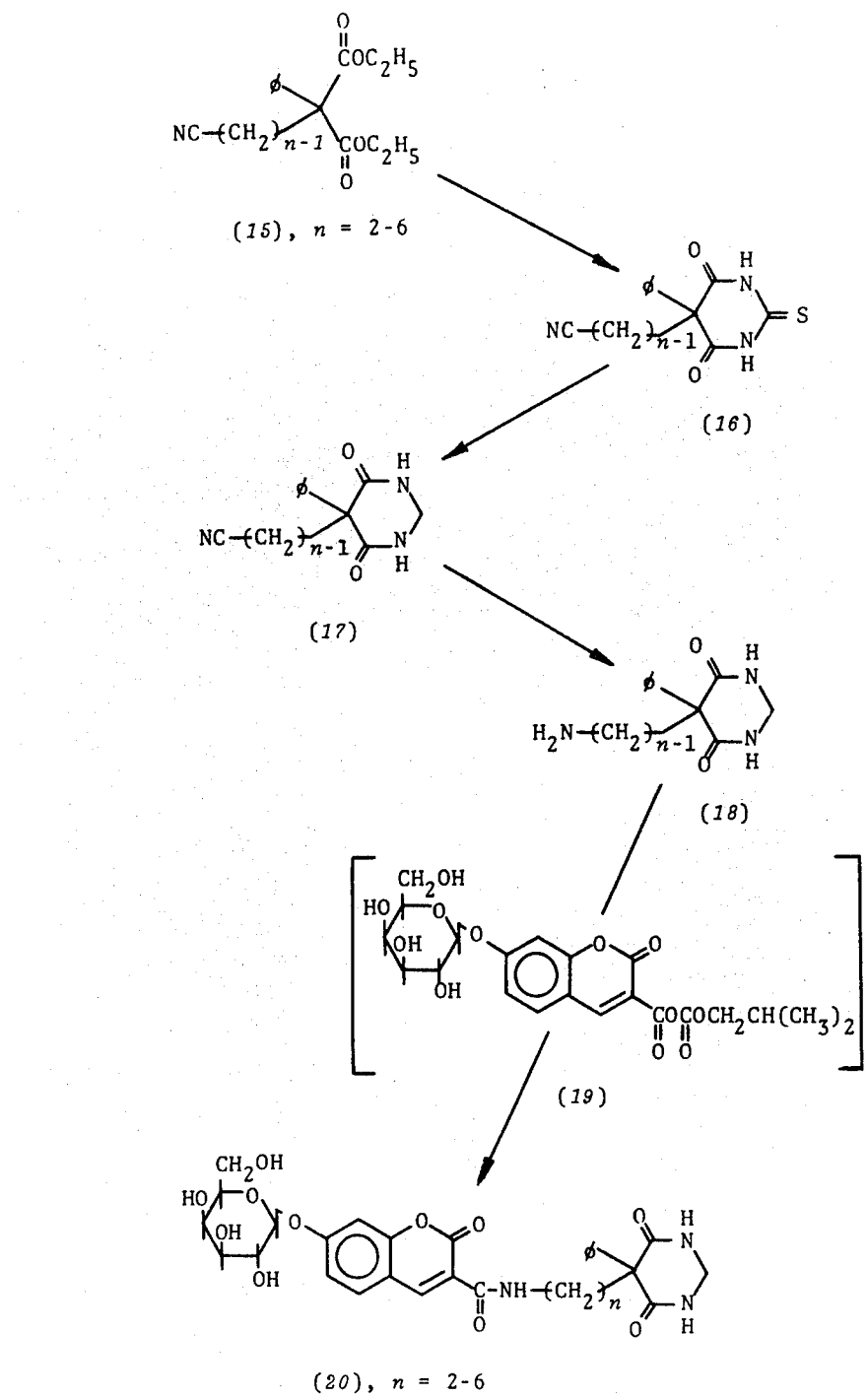
TABLE E

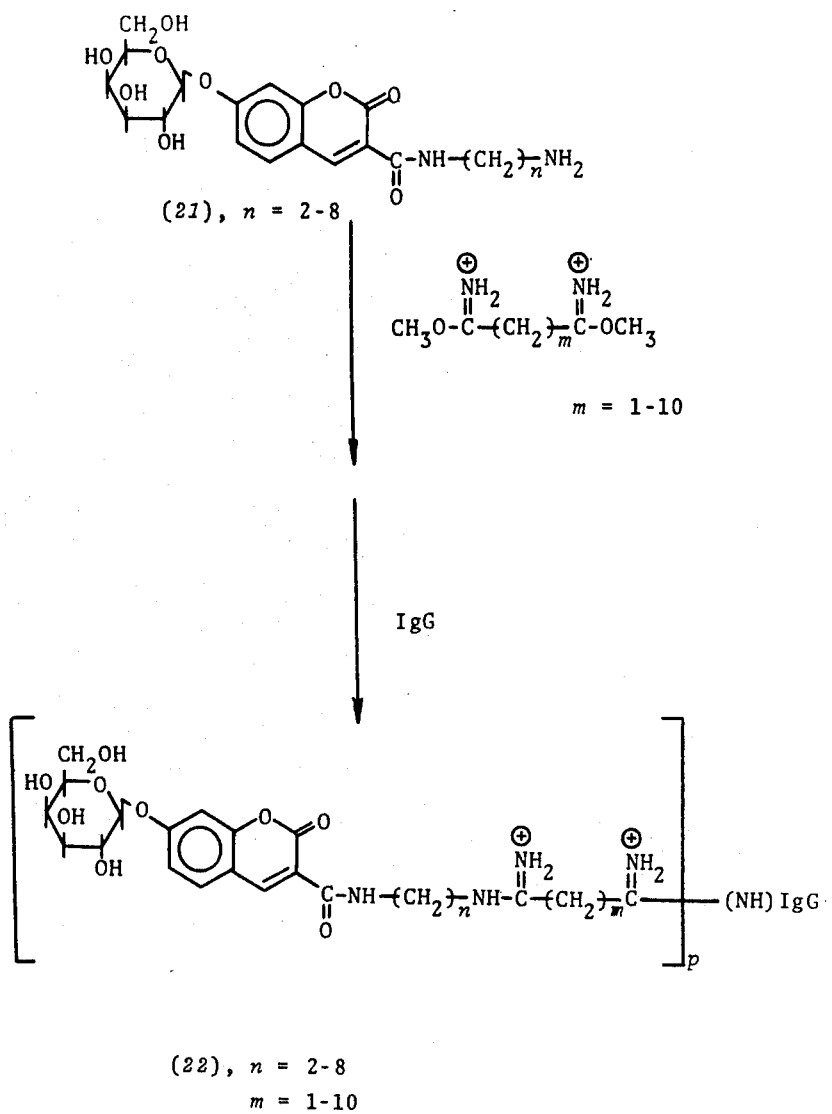
TABLE F

BETA-GALACTOSYL-UMBELLIFERONE-LABELED HAPTEN CONJUGATES

CROSS-REFERENCE TO RELATED APPLICATION

This is a division of application Ser. No. 147,339, filed May 6, 1980, U.S. Pat. No. 4,331,590, which is a division of application Ser. No. 87,819, filed Oct. 23, 1979, U.S. Pat. No. 4,279,992, which is a continuation-in-part of application Ser. No. 886,094, filed Mar. 13, 1978, U.S. Pat. No. 4,226,978.

BACKGROUND OF THE INVENTION

1. Field of the Invention

This invention relates to assay methods, and reagent means for use therein, of the homogeneous and heterogeneous specific binding type for determining qualitatively or quantitatively a ligand in a liquid medium. In particular, the invention relates to an improved nonradioisotopic binding assay employing a novel enzyme substrate label.

2. Description of the Prior Art

In German Offenlegungschriften Nos. 2,618,419 and 2,618,511, corresponding respectively to U.S. patent applications Ser. Nos. 667,982 now abandoned and 667,996, both filed Mar. 18, 1976 and assigned to the present assignee, there are described homogeneous and heterogeneous specific binding assays employing an enzyme-cleavable substrate label. In exemplified embodiments there are disclosed the use of fluorogenic-labeled conjugates comprising umbelliferone or fluorescein coupled via an ester group to a ligand under assay or to a binding partner therefor. The amount of labeled conjugate in the bound-species and/or free-species resulting from the binding reaction system employed is determined by addition of an esterase which cleaves the ester group linking the umbelliferone or fluorescein residue to the ligand or binding partner to release the free fluorescent products, umbelliferone and fluorescein, respectively. The rate of fluorescence production, which follows the rate of release of the fluorescent product, is a function of the amount of ligand in the liquid medium tested.

Performance of this assay depends upon the ability to determine the amount of labeled conjugate which results in either the bound-species or the free-species relative to the amount initially introduced. Where the measured character of the labeled conjugate in the bound-species is essentially indistinguishable from that in the free-species, the two species must be physically separated in order to complete the assay. This type of binding assay follows what is conventionally known as a "heterogeneous" format. On the other hand, where the measured character of the labeled conjugate in the two species is distinguishable, a "homogeneous" format can be followed if desired and the separation step avoided.

While the above described binding assays employing an enzyme-cleavable substrate label offer a generic, novel approach to the pertinent art, the application of the assays to the detection of ligands in certain types of liquid media using the ester linked labeled conjugate is restricted. For example, the ester based assay has been found to be inconvenient for the detection of ligands appearing in the milligram per liter concentration range in physiological fluids such as serum and plasma. It has been found in this situation that the fluid under assay can contain a high endogenous esterase activity and, independently, the ester linked conjugate can exhibit a significant instability as the result of background hydrolysis under the conditions of the assay, which are usually alkaline.

SUMMARY OF THE INVENTION

It has now been found that the specific binding assay employing an enzyme-cleavable substrate label is greatly improved by the use of the novel label component described herein in formation of the labeled conjugate. According to the previously described assay method, the liquid medium under assay for a particular ligand is combined with reagent means, including a conjugate having a label component and a binding component, to form a binding reaction system having a bound-species and a free-species of such labeled conjugate, the label component of the conjugate comprising an enzyme-substrate active portion and an indicator portion, whereby the conjugate is cleavable by an enzyme to produce a detectable indicator product. The resulting bound-species and/or the free-species is contacted with the cleaving enzyme and the resulting indicator product measured as a function of the presence or amount of the ligand to be determined in the liquid medium assayed.

The present improvement comprises employing as the label component of the conjugate, a residue of the formula:

wherein G is a glycone, D is a dye indicator moiety, and R is a linking group through which the dye indicator moiety is covalently bound to the binding component of the conjugate. The cleaving enzyme employed to monitor the label in the bound-species or free-species accordingly is one capable of cleaving the glycosidic linkage between the glycone and the dye indicator moiety. The most preferred glycone and dye indicator moiety for the labeled conjugate are, respectively, a β-galactosyl group and an umbelliferone residue. The assay is adaptable to the detection of any specifically bindable ligand and is particularly useful in the detection of haptens, such as drugs, and antigenic proteins and polypeptides, including antibodies.

In a particularly preferred embodiment, the present invention provides a homogeneous specific binding assay method for determining a ligand in a liquid medium, wherein the liquid medium is combined with (1) a labeled conjugate comprising the ligand or a binding analog thereof coupled to a label component, which label component comprises an enzyme substrate-active portion and an indicator portion whereby the labeled conjugate is cleavable by an enzyme to produce a detectable indicator product, (2) a specific binding partner of the ligand, the labeled conjugate being inactive as a substrate for the enzyme when bound by the binding partner of the ligand, and (3) the cleaving enzyme, and wherein the resulting indicator product is measured as a function of the amount of the ligand in the liquid medium, the improvement comprising employing as the label component of the conjugate, a residue having the formula:

wherein G is a β-galactosyl group, D is a dye indicator moiety, and R is a linking group through which the dye indicator moiety is covalently bound to the ligand or analog thereof, and employing β-galactosidase as the cleaving enzyme whereby the β-galactosyl group may be cleaved to release a detectable dye product.

In an alternative preferred embodiment, the present invention provides a homogeneous specific binding assay method for determining a ligand in a liquid medium, wherein the liquid medium is combined with (1) a labeled conjugate comprising a specific binding partner of the ligand coupled to a labeled component, which label component comprises an enzyme substrate-active portion and an indicator portion whereby the labeled conjugate is cleavable by an enzyme to produce a detectable indicator product, the labeled conjugate being inactive as a substrate for the enzyme when bound by the ligand, and (2) the cleaving enzyme, and wherein the resulting indicator product is measured as a function of the amount of the ligand in the liquid medium, the improvement comprising employing as the label component of the conjugate, a residue having the formula:

G—D—R wherein G is a β-galactosyl group, D is a dye indicator moiety, and R is a linking group through which the dye indicator moiety is covalently bound to the binding partner, and employing β-galactosidase as the cleaving enzyme whereby the β-galactosyl group may be cleaved to release a detectable dye product.

The present invention also provides reagent means and labeled conjugates for use in carrying out the improved assay method.

The presently improved assay method and means feature the advantages of involving a cleaving enzyme for which negligible, if any, endogenous activity is found in physiological fluids such as serum and plasma, and of employing a labeled conjugate wherein the cleavable linkage is very stable under assay conditions in the absence of enzyme. For these reasons the present invention offers a significantly more accurate and reproducible assay than that previously known in the art. Further, antibody-induced hydrolyis of the cleavable linkage, which hydrolysis is sometimes found using the ester-linked labeled conjugates, is absent using the present glycosidic-linked conjugates. Even further, the reagents necessary for performing the assay generally exhibit greater stability, particularly the labeled conjugate, than prior reagents. The glycosidase enzymes involved in the present invention generally are stable over long storage periods and in dilute solutions.

BRIEF DESCRIPTION OF THE DRAWINGS

FIG. 1 is a schematic representation of the basic principles of a specific binding assay employing an enzyme-cleavable substrate label as applied to the immunoassay determination of a drug wherein the cleaved product is fluorescent.

FIG. 2 is a graphical representation of the effect of increasing antibody concentration on the rate of release of cleaved product from a labeled conjugate for use in an assay for gentamicin as described in Example 1.

Figure 3:
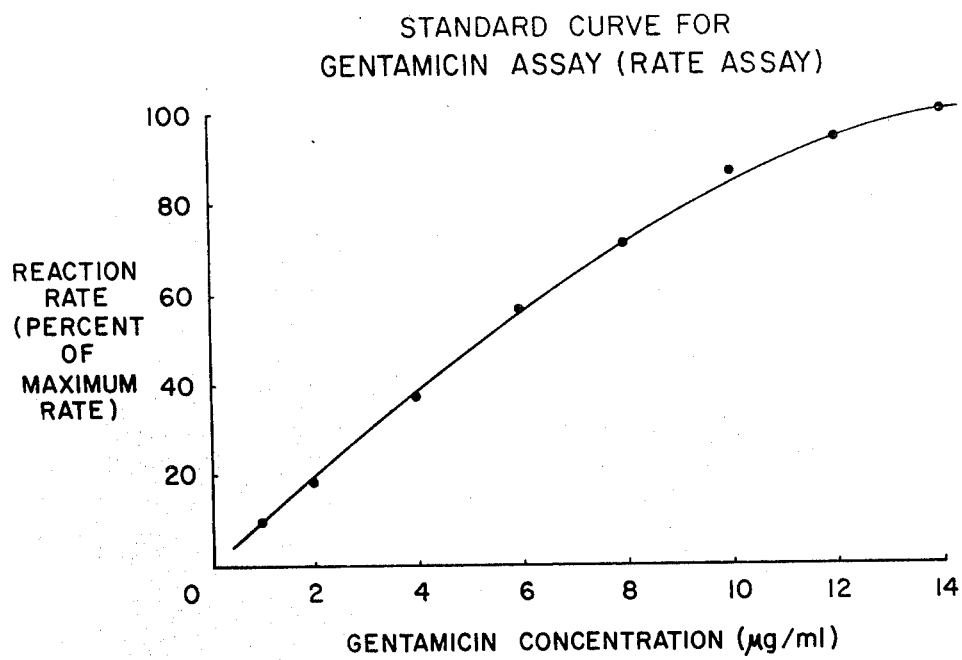
FIG. 3 is a graphical representation of the relation between gentamicin concentration and reaction rate as determined using standards as described in Example 1 for use as a standard curve in a rate assay for gentamicin.

| FIG. | Ligand Assayed |
| --- | --- |
| 4 | Gentamicin |
| 5 | Sisomicin |
| 6 | Netilmicin |
| 7 | Tobramycin |
| 8 | Kanamycin |
| 9 | Amikacin |
| 10 | Diphenylhydantoin |
| 11 | Phenobarbital |
| 12 | Theophylline |
| 13 | Carbamazepine |
| 14 | Primidone |
| 15 | IgG |

Tables A through F are flow diagrams of synthetic schemes described in the examples.

DESCRIPTION OF THE PREFERRED EMBODIMENTS

In the context of this disclosure, the following terms shall be defined as follows: "ligand" is the substance, or class of related substances, whose presence or the amount thereof in a liquid medium is to be determined; "specific binding partner of the ligand" is any substance, or class of substances, which has a specific binding affinity for the ligand to the exclusion of other substances; "specific binding analog of the ligand" is any substance, or class of substances, which behaves essentially the same as the ligand with respect to the binding affinity of the specific binding partner for the ligand; "monitoring reaction" is the reaction in which the glycosidic linkage in the labeled conjugate is cleaved enzymatically to release a detectable indicator product; "lower alkyl" is an alkyl group comprising from 1 to 6 carbon atoms, inclusive, such as methyl, ethyl, isopropyl, and hexyl.

Label Residue

In the novel label residue of the present invention, the glycone may be any group which constitutes the carbohydrate portion of a glycoside. In general, therefore, the glycone is a sugar residue bound through an acetal linkage to the dye indicator moiety in the labeled conjugate. The sugar residue may be selected from residues of monosaccharides, including the aldo-, keto-, deoxy-, and derivatized forms of the trioses, tetroses, pentoses, hexoses and heptoses in their D- or L-stereoisomeric forms; oligosaccharides, such as disaccharides and trisaccharides; and polysaccharides. Where the acetal linkage to the dye indicator moiety is adjacent to an anomeric carbon in the glycone, both the α- and β-stereoconfigurations may be used. It is preferred that the glycone be a monosaccharide such as a pentose, e.g., ribose, arabinose, xylose, and lyxose, with hexoses being particularly preferred, e.g., galactose, glucose, mannose, and gulose. Derivatized monosaccharide residues which may be used include, without limitation, amino-substituted sugars, e.g., glucosamine and galactosamine, O-acyl and O-methyl derivatives, and glucuronides. It is contemplated that oligo- and polysaccharides and their derivatives may be used as well, e.g., the disaccharide cellobiose.

The most preferred group from which the glycone is selected consists of galactosyl, particularly α-and β-D-galactosyl; glucosyl, particularly α- and β-D-glucosyl; N-acetyl-galactosaminyl, particularly N-acetyl-α- or N-acetyl-β-D-galactosaminyl; N-acetyl-glucosaminyl, particularly N-acetyl-α- and N-acetyl-β-glucosaminyl; glucuronyl, particularly β-D-glucuronyl; arabinosyl, particularly α-L-arabinosyl; fucosyl, particularly β-L-fucosyl; mannosyl, particularly α-D-mannosyl; and xylosyl, particularly β-D-xylosyl. The most preferred glycone is a β-galactosyl group.

Dye Indicator Moiety

With regard to the dye indicator moiety in the novel label residue of the present invention, this moiety may comprise any constitutent, usually one containing an organic nucleus especially of aromatic character, couplable to the glycone through a glycosidic linkage and to the binding component of the labeled conjugate through a suitable linking group, such that upon cleavage of such glycoside linkage by an enzyme appropriate for the glycone, there results a detectable dye product distinguishable from the intact labeled conjugate. Preferably the dye indicator moiety is of a type such that the detectable dye product of the enzymatic cleavage is fluorometrically or colorimetrically active. The desired distinctive indicator property of the cleaved product is obtained, in general, by linking the glycone and the dye indicator moiety at a site on the nucleus of the latter such that the fluorogenic or chromogenic character of the cleaved dye product is distinct from that of the intact labeled conjugate. For example, the fluorogenic and chromogenic characters of many known aromatic dyes can be altered by modifying an aryl hydroxyl group. Such a group provides an available site for linkage to the glycone through a glycosidic linkage which upon enzymatic cleavage results in release of a dye product having a fluorogenic or chromogenic character similar to that of the aromatic dye before formation of the labeled conjugate. Usually the fluorescence spectrum of the dye indicator moiety in the labeled conjugate will be shifted from that of the aromatic dye itself. The cleavage reaction is shown schematically below wherein

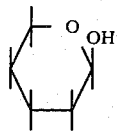

would represent the sugar precursor of the glycone with only the anomeric hydroxyl group specifically shown, A is an aryl nucleus, R is the linking group and L is the binding component of the labeled conjugate:

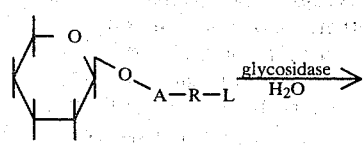

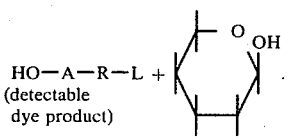

Examples of dyes useful for incorporation into the labeled conjugate of the present invention as the dye indicator moiety are umbelliferone, fluorescein, naphthol, indole, pyridol and resorufin, and active derivatives thereof. Following in Table 1 are representative labeled conjugates comprising residues of such dyes which are contemplated for use in the present invention. G(O— represents the glycone terminating in a bridging oxygen atom which forms a part of the acetal linkage with the dye indicator moiety and—R—L represents a linking group and the linked binding component for the conjugate.

TABLE 1

| dye residue | structural formula |
|---|---|
| umbelliferone [wherein one of $R^1$ and $R^2$ is —R—L and the other is hydrogen or methyl] | |
| fluorescein [wherein $R^3$ is hydroxyl or —(O)G] | |
| 3-indole | |
| naphthol | |
| pyridol | |
| resorufin | |

Other variations of labeled conjugates based on the above listed dye residues are clearly evident. Various derivatives, particularly in the nature of aryl substituted derivatives, which retain sufficient ability to be coupled to the glycone and binding component and to exhibit appropriate fluorogenic or chromogenic character in the cleaved indicator product can be used in preparing labeled conjugates. Labeled conjugates which are prepared using such a substituted dye as starting material will possess substantially the same properties as the conjugates prepared from the abve-listed dyes. Such conjugates will be recognized as equivalents and are exemplified by addition of one, two or more simple substituents to an available aromatic ring site, such substituents including without limitation lower alkyl, e.g., methyl, ethyl and butyl; halo, e.g., chloro and bromo; nitro; carboxyl; carbo lower alkoxy, e.g., carbomethoxy and carbethoxy; amino; mono- and di-lower alkylamine, e.g., methylamino, dimethylamino and methylethylamino; amido; hydroxyl; lower alkoxy, e.g., methoxy and ethoxy; and so forth.

The preferred dye indicator moiety is an umbelliferone residue which is bound directly to the glycone by an acetal linkage at the 7-position and bound to the binding component through a linking group at the 3 or 4-position, preferably the former. Especially useful are labeled conjugates, comprising such an umbelliferone residue coupled to a β-galactosyl group as the glycone at the 7-position and to the binding component through the 3-position. Such conjugates are represented as:

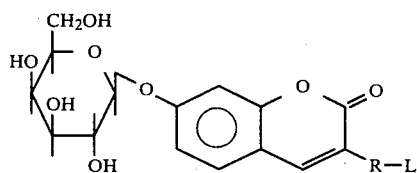

wherein R is a linking group and L is the binding component such as a hapten of molecular weight between 100 and 1000 or an antigenic protein or polypeptide of molecular weight between 1,000 and 10,000,000.

Linking Group

It will be recognized that there are many methods available for linking the binding component of the labeled conjugate, e.g., the ligand to be detected, a binding analog thereof, or a binding partner thereof, to the dye indicator moiety. The particular chemical character of the linking group will depend upon the nature of the respective available linking sites on the binding component and the dye indicator moiety. The important considerations in selecting the linking sites are (1) preservation of the ability of the linked binding component to participate effectively in the selected binding assay system and (2) preservation of the ability of the linked dye indicator moiety upon enzymatic cleavage to yield an effectively detectable product, in both cases, to the extent that a useful assay will result for the particular ligand under assay and for the particular concentrations or amounts in which such ligand is to be detected. Usually the linking group will comprise a chemical bond, usually a single, but sometimes a double bond, or a chain containing between 1 to 10, more commonly 1 to 6, carbon atoms and 0 to 5, more commonly 1 to 3, heteroatoms selected from nitrogen, oxygen, and sulfur.

Both the dye indicator moiety and the binding component, of course, will offer a great diversity of available functionalities for attachment of the linking group. Commonly the functionalities that can be expected to be available to the linking group are amines, usually amino; hydroxyl; halo, usually chloro or bromo; carboxylic acid; aldehyde; keto; isothiocyanate; isocyanate; and so forth. Accordingly, the chemical structure of the linking group itself will vary widely with its terminal groups depending on the functionalities available on the dye indicator moiety and the binding component and its overall length being a matter of choice within the basic constraint of maintaining the essential enzymatic substrate and binding component characters of the resulting conjugate. With regard to the length of the linking group in preparing a conjugate for use in a homogeneous assay format, it is usually desirable to use as short a group as possible without causing the resulting binding component in the conjugate to interfer significantly with the substrate activity of the conjugate. Where the binding component is of low molecular weight (e.g., a hapten of molecular weight between 100 and 1000), the linking group is preferably a chemical bond or a 1 to 3 atom chain such as carbonyl, amido, and the like. In other circumstances, such as where the binding component in the conjugate is of relatively high molecular weight, such as a polypeptide or protein (e.g., an antibody), a longer linking group is usually desirable to prevent steric hindrance of the substrate-active site of the conjugate. In these cases, the linking group will comprise usually 4 to 10 carbon atoms and 0 to 5 heteroatoms as previously discussed. Chains of any significantly greater length will tend to result in conjugates in which the binding component will tend to fold-back into the substrate-active site. With these considerations in mind, examples of linking groups are shown in Table 2. Particular examples of linking groups will be seen hereinafter and further variations will be readily recognized as being state-of-the-art.

TABLE 2 linking group

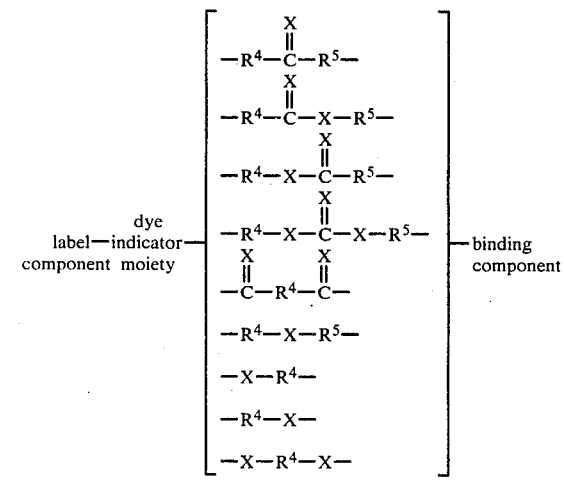

wherein X is imino, sulfur or, preferably, oxygen; and $R^4$ and $R^5$ are, independently, a bond or lower alkylene such as methylene, ethylene, butylene or hexylene.

The present assay can be applied to the detection of any ligand for which there is a specific binding partner. The ligand usually is a peptide, protein, carbohydrate, glycoprotein, steroid, or other organic molecule for which a specific binding partner exists in biological systems or can be synthesized. The ligand, in functional terms, is usually selected from the group consisting of antigens and antibodies thereto; haptens and antibodies thereto; and hormones, vitamins, metabolites and pharmacological agents, and their receptors and binding substances. Specific examples of ligands which can be detected using the present invention are hormones such as insulin, chorionic gonadotropin, thyroxine, liothyronine, and estriol; antigens and haptens such as ferritin, bradykinin, prostaglandins, and tumor specific antigens; vitamins such as biotin, vitamin $B_{12}$, folic acid, vitamin E, vitamin A, and ascorbic acid; metabolites such as 3',5' adenosine monophosphate and 3',5' guanosine monophosphate; pharmacological agents or drugs, particularly those described below; antibodies such as microsomal antibody and antibodies to hepatitis and allergens; and specific binding receptors such as thyroxine binding globulin, avidin, intrinsic factor, and transcobalamin. The present assay is particularly useful for the detection of haptens, and analogs thereof, of molecular weight between 100 and 1000, particularly drugs and their analogs, including the aminoglycoside antibiotics such as streptomycin, neomycin, and especially gentamicin, tobramycin, amikacin, kanamycin, sisomicin, and netilmicin; anticonvulsants such as diphenylhydantoin, phenobarbital, primidone, carbamazepine, ethosuximide, and sodium valproate; bronchodialators such as theophylline; cardiovascular agents such as quinidine, procainamide and propanolol; drugs of abuse such as morphine, barbiturates and amphetamines; tranquilizers such as valium and librium; and various other drugs, including amitriptyline, cortisol, cyclophosphamide, desipramine, disopyramide, doxepin, doxorubicin, imipramine, lidocaine, methotrexate and nortriptyline.

As stated previously, the present assay method can follow, in appropriate circumstances, either a homogeneous or a heterogeneous scheme.

HOMOGENEOUS SCHEMES

A homogeneous scheme, i.e., one which does not require a physical separation of the bound-species and the free-species, is available where reaction between the binding component of the labeled conjugate and a corresponding binding partner causes a measurable change, either in a positive or a negative sense, in the ability of the label component of the labeled conjugate to participate in the monitoring reaction, i.e., in the ability of the labeled conjugate to be cleaved enzymatically to release the detectable product. In such a case, the distribution of the label component between the bound-species and the free-species can be determined by adding the enzyme directly to the binding reaction mixture and measuring therein the activity of the substrate-active label component, i.e., the rate or total amount of detectable product that results, which preferably comprises measuring the rate of fluorescence or color production or the total amount thereof produced. Several manipulative schemes are available for carrying out a homogeneous assay with preference being given to the direct binding and competitive binding techniques.

Briefly, in the direct binding technique, a liquid medium suspected of containing the ligand to be detected, usually a compound of high molecular weight (e.g., an antibody) relative to a selected binding partner (e.g., an antigen or hapten), is contacted with the present labeled conjugate in which the binding component is the selected specific binding partner of the ligand, and thereafter any change in the substrate activity of the label component is assessed. In the competitive binding technique, primarily useful for the detection of a compound of low molecular weight (e.g., an antigen or hapten) relative to a selected binding partner (e.g., an antibody), the liquid medium is contacted with the selected specific binding partner of the ligand and with the present labeled conjugate in which the binding component is one of the ligand or a specific binding analog thereof, and thereafter any change in the substrate activity of the label component is assessed. In both techniques, the substrate activity of the label component is determined by contacting the liquid medium with an enzyme which can cleave the glycosidic linkage in the label component of the free-species form of the labeled conjugate and then measuring the rate or amount of detectable product which results. Qualitative determination of the ligand in the liquid medium involves comparing a characteristic, usually the rate, of the resulting reaction to that of the monitoring reaction in a liquid medium devoid of the ligand, any difference therebetween being an indication of the presence of such ligand in the liquid tested. Quantitative determination of the ligand in the liquid medium involves comparing a characteristic of the resulting reaction to that of the monitoring reaction in liquid media containing various known amounts of the ligand, e.g., a comparison to a standard curve.

A schematic representation of the principles of a competitive binding type of homogeneous immunoassay for a drug is shown in FIG. 1 of the drawing. As shown, the free labeled drug is acted upon by the enzyme to release a fluorescent product. However, upon addition of antibody to the drug, the action of the enzyme on the resulting labeled drug-antibody complex is inhibited, probably by steric hindrance. In the competitive binding reaction then, the ability of the enzyme to release the fluorescent product is dependent upon the ratio of labeled drug remaining free to that bound to antibody. Thus, the reaction rate of production of fluorescence is proportional to the amount of drug to be assayed which competes with labeled drug for antibody binding.

In general, when following a homogeneous assay scheme, the components of the specific binding reaction, i.e., the liquid medium suspected of containing the ligand, the labeled conjugate, and, in some systems, a specific binding partner of the ligand, may be combined in any amount, manner, and sequence, provided that the activity of the label component of the labeled conjugate is measurably altered when the liquid medium contains the ligand in an amount or concentration of significance to the purposes of the assay. Preferably, all of the components of the specific binding reaction are soluble in the liquid medium.

Known variations of the above briefly described homogeneous methods and further details concerning the specific techniques discussed are readily available in the literature, e.g., German OLS No. 2,618,511, corresponding to U.S. patent application Ser. No. 667,996, filed Mar. 18, 1976, now abandoned, and assigned to the present assignee.

HETEROGENEOUS SCHEMES

The use of the present novel substrate-active labels can also be applied to the conventional heterogeneous type assay schemes wherein the bound- and free-species of the labeled conjugate are separated and the quantity of label in one or the other is determined. The reagent means for performing such a heterogeneous assay can take on many different forms. In general, such means comprises three basic constituents, which are (1) the ligand to be detected, (2) a specific binding partner of the ligand, and (3) the labeled conjugate. The binding reaction constituents are combined simultaneously or in a series of additions, and with an appropriate incubation period or periods, the labeled conjugate becomes bound to its corresponding binding partners such that the extent of binding, i.e., the ratio of the amount of labeled conjugate bound to a binding partner (the "bound-species") to that unbound (the "free-species"), is a function of the amount of ligand present. The bound- and free-species are physically separated and the amount of label present in one thereof is compared to a negative control or standard results, e.g., a standard curve.

Various means of performing the separation step and of forming the binding reaction systems are available in the art. Separation can involve such conventional techniques as those involving what is commonly known as a solid-phase antibody or antigen, a second antibody, or a solid phase second antibody, as well as the use of immune complex precipitating agents and adsorbents, and so forth. Binding reaction systems that can be followed include the so-called competitive binding technique, the sequential saturation technique, the "sandwich" technique, and so forth. Further details concerning the various known heterogeneous systems are readily available in the literature, e.g., German OLS No. 2,618,419, corresponding to U.S. patent application Ser. No. 667,982, filed Mar. 18, 1976, now abandoned, and assigned to the present assignee.

It should be recognized that manipulative schemes involving other orders of addition and other binding reaction formats can be devised for carrying out homogeneous and heterogeneous specific binding assays without departing from the inventive concept embodied herein.

The liquid medium to be tested can be a naturally occurring or artificially formed liquid suspected of containing the ligand, and usually is a biological fluid or a liquid resulting from a dilution or other treatment thereof. Biological fluids which can be assayed following the present method include serum, plasma, urine, saliva, and amniotic, cerebral, and spinal fluids. Other materials such as solid matter, for example tissue, or gases can be assayed by reducing them to a liquid form such as by dissolution of the solid or gas in a liquid or by liquid extraction of the solid.

In general, in those instances where for purposes of a selected binding assay system the binding component in the labeled conjugate is the ligand or an analog thereof, the present labeled conjugate can be termed a glyconedye-labeled ligand and can be represented by the formula:

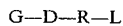

G—D—R—L wherein G, D and R have their meanings as hereinabove and L is the ligand or analog thereof, usually a hapten or an antigenic protein or polypeptide. A polypeptide is conventionally defined as a polymer of amino acids joined by amide linkages, forming chains that can consist of as few as two or as many as several thousand amino acid residues.

As discussed previously herein, the preferred labeled conjugates comprise an umbelliferone residue coupled to a β-galactosyl group by an acetal linkage at the 7-position and bound to the binding component through the 3-position. In the usual case, the binding component will be a hapten, usually of molecular weight between 100 and 1,000, or an antigenic protein or polypeptide, usually of molecular weight between 1,000 and 10,000,000. Such hapten or antigenic protein or polypeptide will be a ligand of clinical interest, whereby the label component is bound directly thereto, or a derivative of a ligand of clinical interest, whereby the label component is bound through a bridge group.

The preferred β-galactosyl-umbelliferone labeled conjugates are prepared by first obtaining the intermediate of the formula:

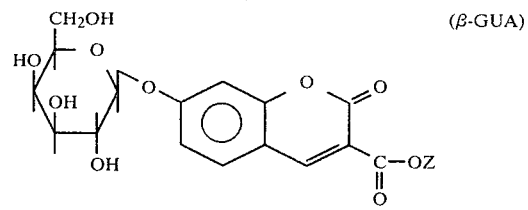

(β-GUA)

wherein Z is hydrogen or a suitable salt cation such as potassium or sodium, by reaction of 3-carboethoxyumbelliferone and tetraacetyl-α-D-galactosyl bromide followed by hydrolysis according to the method of Leaback, *Clin. Chem. Acta* 12:647(1965). The compound to be labeled (either the ligand of analytical interest or a derivative thereof) is selected to have an amino or carboxyl group available for coupling to the β-GUA intermediate by formation of a peptide or amide bond.

Condensation of the β-GUA intermediate to the compound to be labeled can be accomplished by reacting the β-GUA intermediate directly with an amino group-containing ligand or derivative thereof using conventional peptide condensation reactions such as the carbodiimide reaction [*Science* 144:1344(1964)], the mixed anhydride reaction [Erlanger et al, *Methods in Immunology and Immunochemistry*, ed. Williams and Chase, Academic Press (New York 1967) p. 149], and the acid azide and active ester reactions [Kopple, *Peptides and Amino Acids*, W. A. Benjamin, Inc. (New York 1966)]. See also for a general review *Clin. Chem.* 22:726(1976).

It will be recognized, of course, that other well known methods are available for coupling the compound to be labeled to the β-GUA intermediate. In particular, conventional bifunctional coupling agents can be employed for coupling a ligand, or its derivative, containing a carboxylic acid or amino group to the β-GUA intermediate. For example, appropriate coupling reactions are well known for inserting a bridge group in coupling an amine to a carboxylic acid. Coupling reactions of this type are thoroughly discussed in the literature, for instance in the above-mentioned Kopple monograph and in Lowe and Dean, *Affinity Chromatography*, John Wiley & Sons (New York 1974). Such coupling techniques will be considered equivalents to the previously discussed peptide condensation reactions in preparing useful labeled conjugates. The choice of coupling technique will depend on the functionalities available in the compound to be labeled for coupling to the β-GUA intermediate and on the length of bridging group desired.

General methods for coupling antigenic proteins and polypeptides and haptens to the β-GUA intermediate will now be described.

Proteins and Polypeptides

The β-galactosyl-umbelliferone-labeled conjugates will have the formula:

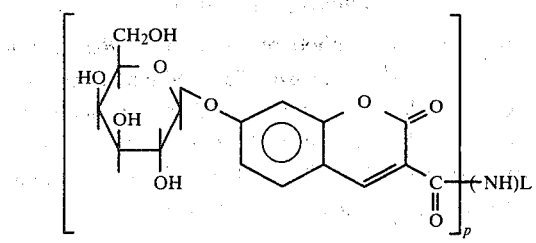

wherein —(NH)L is an antigenic protein or polypeptide bound through an amide bond and p=1 to the number of available amino groups in L.

Representative of specifically bindable protein ligands are antibodies in general, particularly those of the IgG, IgE, IgM and IgA classes, for example hepatitis antibodies; and antigenic proteins such as insulin, chorionic gonadotropin (e.g., HCG), carcinoembryonic antigen (CEA), myoglobin, hemoglobin, follicle stimulating hormone, human growth hormone, thyroid stimulating hormone (TSH), human placental lactogen, thyroxine binding globulin (TBG), instrinsic factor, transcobalamin, enzymes such as alkaline phosphatase and lactic dehydrogenase, and hepatitis-associated antigens such as hepatitis B surface antigen ($HB_sAg$), heptatitis B e antigen ($HB_eAg$) and hepatitis B core antigen ($HB_cAg$). Representative of polypeptide ligands are angiotensin I and II, C-peptide, oxytocin, vasopressin, neurophysin, gastrin, secretin, and glucagon.

Since, as peptides, ligands of this general category possess numerous available carboxylic acid and amino groups, coupling to the β-GUA intermediate can proceed according to conventional peptide condensation reactions such the carbodiimide reaction, the mixed anhydride reaction, and so forth as described hereinabove, or by the use of conventional bifunctional reagents likewise as described above. General references concerning the coupling of proteins to primary amines or carboxylic acids are mentioned in detail above.

Haptens

The β-galactosyl-umbelliferone-labeled conjugates will have the formula:

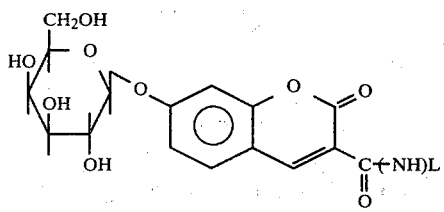

wherein —(NH)L is a hapten bound through an amide bond.

Haptens, as a class, offer a wide variety of organic substances which evoke an immunochemical response in a host animal only when injected in the form of an immunogen conjugate comprising the hapten coupled to a carrier molecule, almost always a protein such as albumin. The coupling reactions for forming the immunogen conjugates are well developed in the art and in general comprise the coupling of a carboxylic acid or amino group-containing hapten or a carboxylic acid or amino derivative of the hapten to available amino or carboxylic acid groups on the protein carrier by formation of an amide bond. Such well known coupling reactions are directly analogous to the present formation of labeled conjugates by coupling carboxylic acid or amino group-containing haptens or hapten derivatives to the β-GUA intermediate.

Hapten ligands which themselves contain amino functions, and which thereby can be coupled directly to the β-GUA intermediate, include the iodothyronine hormones such as thyroxine and liothyronine, as well as other materials such as aminoglycoside antibiotics. Following are representative synthetic routes for preparing carboxylic acid and amine analogs of haptens of analytical interest which themselves do not contain an available carboxylic acid or amino function whereby such analogs can be coupled to the β-GUA intermediate by the aforementioned peptide condensation reactions or bifunctional coupling agent reactions (in the structural formulae below, n represents an integer, usually 1 through 6, and Me represents methyl).

Carbamazepine

Dibenz[b,f]azepine is treated sequentially with phosgene, an ω-aminoalkanol, and Jones reagent (chromium trioxide in sulfuric acid) according to the method of Singh, U.S. Pat. No. 4,058,511 to yield a series of carboxylic acids (R*=COOH). The corresponding primary amines (R*=NH$_2$) are obtained by treating dibenz[b,f]azepine sequentially with phosgene and an α,ω-diaminoalkane.

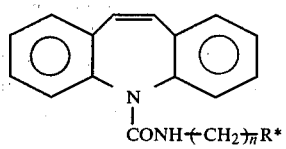

Quinidine

Following the method of Cook et al, *Pharmacologist* 17:219(1975), quinidine is demethylated and treated with ethyl 5-bromovalerate followed by acid hydrolysis to yield a suitable carboxylic acid derivative. The corresponding primary amines can be obtained by any of the conventional methods for converting carboxyl groups to amino groups such as the Hofmann reaction, the Schmidt reaction, and the Curtius reaction [*Organic Reactions*, vol. III, ed. Adams et al, Robert E. Kreiger Publishing Co., Huntington, NY (1975)]. Useful amine derivatives can also be prepared by reacting the carboxylic acid derivative with α,ω-diaminoalkanes to yield ω-aminoalkylamides.

Digoxin and Digitoxin

The aglycone of the cardiac glycoside is treated with succinic anhydride and pyridine according to the method of Oliver et al, *J. Clin. Invest.* 47:1035(1968) to yield a suitable carboxylic acid (R*=COOH). Suitable primary amines (R*=NH$_2$) are obtained by the aforesaid techniques, i.e., the Hofmann, Schmidt, and Curtius reactions or formations of ω-aminoalkylamides.

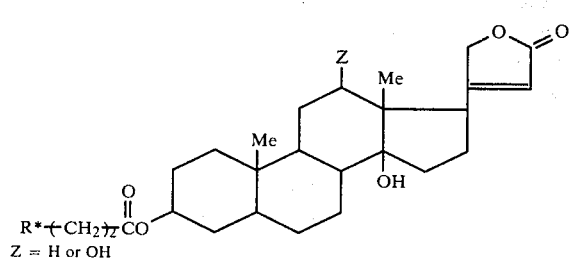
Z = H or OH

Theophylline

Following the method of Cook et al, Res. Comm. Chem. Path. Pharm 13:497(1976), 4,5-diamino-1,3-dimethylpyrimidine-2,6-dione is heated with glutaric anhydride to yield a suitable carboxylic acid (R*=COOH). Suitable primary amines (R*=NH$_2$) are obtained by the aforesaid techniques (cf. Example 9).

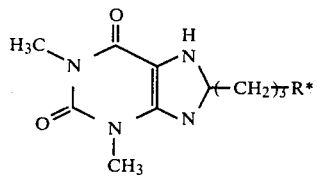

Phenobarbital and Primidone

Sodium phenobarbital is heated with methyl 5-bromovalerate and the product hydrolyzed to the corresponding acid derivative (R*=COOH) of phenobarbital [Cook et al, Quantitative Analytic Studies in Epilepsy, ed. Kelleway and Peterson, Raven Press (New York 1976) pp. 39–58]. Suitable primary amines (R*=NH$_2$) are obtained by the aforesaid techniques.

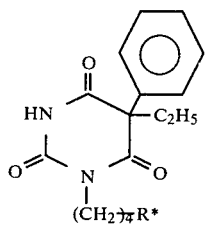

To obtain the acid derivative of primidone following the same Cook et al reference method, 2-thiophenobarbital is alkylated, hydrolyzed, and the product treated with Raney nickel to yield a suitable carboxylic acid (R*=COOH). Again, suitable primary amines (R*=NH$_2$) are obtained by the aforesaid techniques.

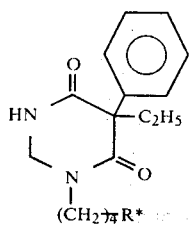

Diphenylhydantoin

Following the method of Cook et al, Res. Comm. Chem. Path. Pharm. 5:767(1973), sodium diphenylhydantoin is reacted with methyl 5-bromovalerate followed by acid hydrolysis to yield a suitable carboxylic acid (R*=COOH). Suitable primary amines (R*=NH$_2$) are obtained by the aforesaid techniques.

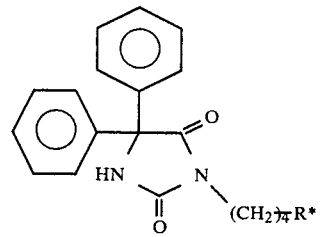

Morphine

Morphine free base is treated with sodium β-chloroacetate according to the method of Spector et al, Science 168:1347(1970) to yield a suitable carboxylic acid derivative. The corresponding primary amine is obtained by the aforesaid techniques.

Nicotine

According to the method of Langone et al, Biochem 12(24):5025(1973), trans-hydroxymethylnicotine and succinic anhydride are reacted to yield a suitable carboxylic acid (R*=COOH). Suitable amines (R*=NH$_2$) are obtained by the aforesaid techniques.

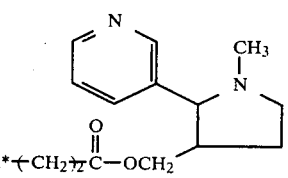

Androgens

Suitable carboxylic acid derivatives (R*=COOH) of testosterone and androstenedione linked through either the 1- or 7-position on the steroid nucleus are prepared according to the method of Bauminger et al, J. Steroid Biochem. 5:739(1974). Suitable amines (R*=NH$_2$) are obtained by the aforesaid techniques.

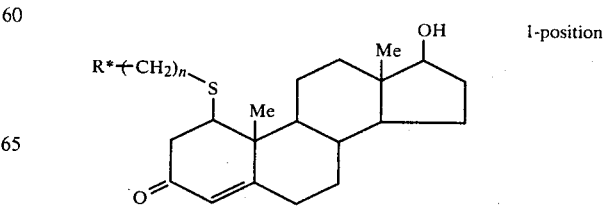

1-position

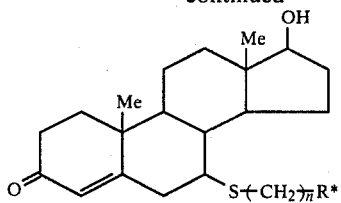

7-position

Estrogens

Suitable carboxylic acid derivatives (R*=COOH) of estrogens, e.g., estrone, estradiol and estriol, are prepared according to the method of Bauminger et al, supra. Suitable amines (R*=NH₂) are obtained by the aforesaid techniques.

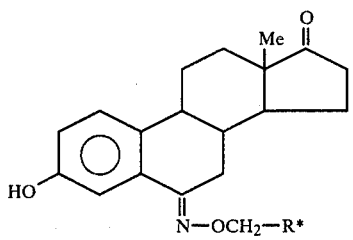

Progesterones

Suitable carboxylic acid derivatives (R*=COOH) of progesterone and its metabolites linked through any of the 3-, 6- or 7-positions on the steroid nucleus are prepared according to the method of Bauminger et al, supra. Suitable amines (R*=NH₂) are obtained by the aforesaid techniques.

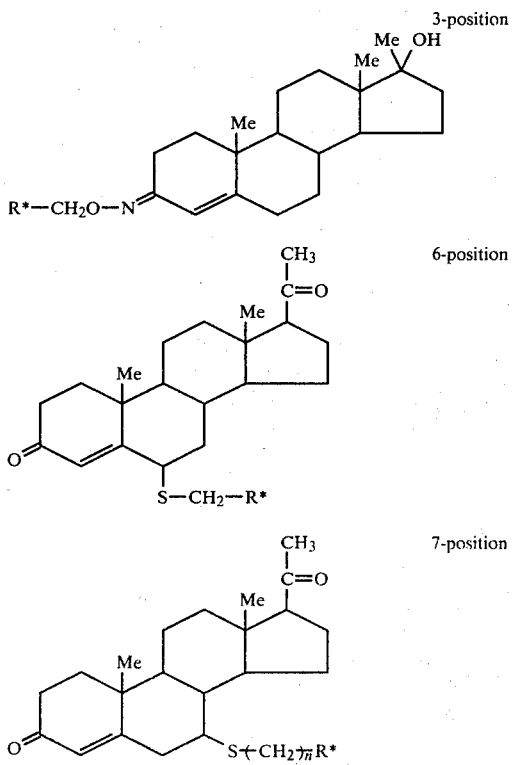

The methods described above are but examples of the many known techniques for forming suitable carboxylic acid and amine derivatives of haptens of analytical interest. The principal derivation techniques for preparing the acids are discussed in Clin. Chem. 22:726(1976) and include esterification of a primary alcohol with succinic anhydride [Abraham and Grover, Principles of Competitive Protein-Binding Assays, ed. Odell and Daughaday, J. B. Lippincott Co. (Philadelphia 1971) pp. 140-157], formation of an oxime from reaction of a ketone group with carboxylmethyl hydroxylamine [J. Biol. Chem. 234:1090(1959)], introduction of a carboxyl group into a phenolic residue using chloroacetate [Science 168:1347(1970)], and coupling to diazotized p-aminobenzoic acid in the manner described in J. Biol. Chem. 235:1051(1960). The corresponding amines are prepared by any of the conventional methods (i.e., the Hofmann, Schmidt, and Curtius reactions, supra) or by reacting the carboxylic acid derivatives with α,ω-diaminoalkanes to yield ω-aminoalkylamides.

The present invention will now be illustrated, but is not intended to be limited by, the following examples.

TABLE OF CONTENTS FOR EXAMPLES

| Example No. | Ligand Assayed | Assay Type |
|---|---|---|
| 1 | Gentamicin | Rate/Fixed-Time |
| 2 | Sisomicin | Rate |
| 3 | Netilmicin | Rate |
| 4 | Tobramycin | Rate |
| 5 | Kanamycin | Rate |
| 6 | Amikacin | Rate |
| 7 | Diphenylhydantoin | Rate |
| 8 | Aminoglycosides | Fixed-Time |
| 9 | Phenobarbital | Fixed-Time |
| 10 | Theophylline | Fixed-Time |
| 11 | Carbamazepine | Fixed-Time |
| 12 | Primidone | Fixed-Time |
| 13 | Immunoglobulins | Fixed-Time |

EXAMPLES 1-6

Aminoglycoside Antibiotic Assays

To perform an assay for an aminoglycoside antibiotic according to the present invention there can be used a labeled conjugate wherein the binding component is said antibiotic under assay or a binding analog thereof. Where an antibody is used as binding partner in the assay, such as in a homogeneous or heterogeneous competitive binding assay, it has been found that other aminoglycoside antibiotics can cross-react with the antibody for the antibiotic under assay. Thus such other antibiotics qualify as binding analogs and could be used to form the labeled conjugate. Further, the antibody qualifies as reagent for use in assays for the cross-reacting antibiotic. For example, in an assay for gentamicin it has been found that with appropriate antiserum the binding component in the labeled conjugate can be gentamicin itself or sisomicin which cross-reacts. Thus, gentamicin antiserum and a labeled sisomicin conjugate could be used in an assay for gentamicin. Specificity problems are not encountered in clinical situations because it would be known what antibiotic was administered and only one aminoglycoside antibiotic is administered at a time.

The β-galactosyl-umbelliferone-labeled conjugates formed are of the formula:

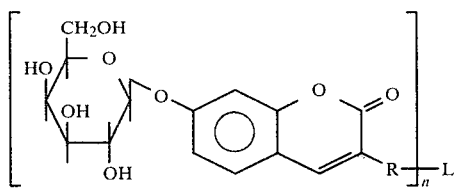

wherein R is a linking group as described hereinbefore terminating in an amino-linking group, preferably carbonyl; L is an aminoglycoside antibiotic selected from the group consisting of gentamicin, tobramycin, amikacin, kanamycin, sisomicin, and netilmicin, coupled by a covalent bond to the linking group R through a primary amino group therein; and n equals 1 to the total number of primary amino groups in the selected antibiotic, inclusive.

EXAMPLE 1

Gentamicin Assays

A. Preparation of glycone-dye-drug conjugate

The reaction sequence for the preparation of the glycone-dye-drug conjugate is given in Table A in the drawings. 3-carboethoxy-7-hydroxycoumarin (II) was prepared by a Knoevenagel condensation of 2,4-dihydroxybenzaldehyde (Aldrich Chemical Co., Milwaukee, Wisconsin, USA) with diethylmalonate in acetic acid, benzene, and piperidine as described in *J. Am Chem. Soc.* 63:3452(1971). The potassium salt of 7-β-galactosylcoumarin-3-carboxylic acid (III) was prepared by the reaction of 3-carboethoxy-7-hydroxycoumarin (II) and 2,3,4,6-tetraacetyl-α-D-galactosyl bromide (I, Sigma Chemical Co., St. Louis, Mo., USA) as described by Leaback for the preparation of methylumbelliferyl-β-D-galactoside in *Clin. Chim. Acta* 12:647 (1965). The potassium salt of this compound was purified by chromatography on silica gel-60 (E. Merck, St. Louis, Mo., USA) with a gradient of n-butanol/methanol/water (4/2/1 by volume) and methanol/water (1/6). After recrystallization from acetone-water, the corrected melting point of the product was 258°–263° C. (decomp.).

Analysis: Calculated for $C_{16}H_{15}O_{10}K$: C, 47,28; H, 3.73; K, 9.62. Found: C, 47.30; H, 3.74; K, 9.34. $[\alpha]_D = -77.4°$ (c 1.0, $H_2O$).

NMR Spectrum ($D_2O$): δ8.2 (s, 1H), 7.6 (m, 1H), 7.0 (m, 2H), 5.1 (s, 1H), and 4.0 (m, 6H).

Infrared Spectrum (KBr): 1705 $cm^{-1}$ (carbonyl), 1620 $cm^{-1}$ (C=C).

β-Galactosyl-umbelliferone-sisomicin (IV) was prepared by mixing 50 milligrams (mg) (117 μmol) of the potassium salt of 7-β-galactosylcoumarin-3-carboxylic acid (III) with 171 mg of sisomicin sulfate (223 μmol of sisomicin free base, Schering Corp., Bloomfield, N.J., U.S.A.) in 2 ml of water. The pH was adjusted to 3.8 by dropwise addition of 1 molar hydrochloric acid. The solution was cooled in an ice bath and 30 mg (150 μmol) of 1-ethyl-3-(3-dimethylaminopropyl)-carbodiimide hydrochloride (Pierce Chemical Co., Rockford, Ill., U.S.A.) was added. After 2 hours the mixture was chromatographed at 25° C. on a 2.5×50 centimeter (cm) column of CM-Sephadex C-25 (Pharmacia Laboratories, Inc., Piscataway, N.J. U.S.A.) 5.8 ml fractions were collected, and their absorbance was monitored at 345 nanometers (nm). The column was washed with 200 ml of 50 mmol/liter ammonium formate to elute unreacted 7-β-galactosylcoumarin-3-carboxylic acid (III). A linear gradient formed with 400 ml of 50 mmol/liter and 400 ml of 1.8 mol/liter ammonium formate, was applied to the column. A peak of material absorbing at 345 nm eluted at approximately 1.4 mol/liter ammonium formate. After the gradient, the column was washed with 600 ml of 1.8 mol/liter ammonium formate. Three 345 nm absorbing peaks were eluted in this wash. Eluted unreacted sisomicin was well separated from the last 345 nm absorbing peak.

The carbodiimide-activated reaction leads to the formation of amide bonds between the carboxylic acid of β-[7-(3-carboxycoumarinoxy)]-galactoside and the primary amino groups of sisomicin. The major peak of β-galactosyl-umbelliferone-sisomicin (the last 345 nm absorbing peak) was used in the present studies. Ammonium formate was removed by lyophilization. Because the absorptivity of isolated labeled conjugate is currently unknown, the relative concentration is presented in terms of $A_{345}$ units. One $A_{345}$ unit is the quantity of material contained in 1 ml of a solution that has an absorbance of 1.0 at 345 nm when measured with a 1 cm light path.

B. Assay Procedure—Rate Assay

The principle of the assay is shown schematically in FIG. 1 of the drawings.

A reagent, prepared in 50 mmol/liter N,N-bis-(2-hydroxyethyl)-glycine (Bicine) buffer (pH 8.2, Nutritional Biochemicals Corp., Cleveland, Ohio, U.S.A.), contained β-galactosidase (25 ng protein/ml, *Escherichia coli*-derived enzyme, Grade IV, Sigma Chemical Co., St. Louis, Mo., U.S.A.) and antiserum to gentamicin (prepared as described in *Nature New Biol.* 239:214 (1972) in an amount sufficient to decrease the reaction rate in the final reagent to 20 to 30% of the rate observed in the absence of antibody). One unit (U) of the enzyme was defined as that amount which hydrolyzed 1.0 μmole of o-nitriphenyl-β-D-galactoside per minute at pH 7.2 at 37° C. The enzyme preparation used had a specific activity of 745 U per milligram of protein.

To 2.0 ml aliquots of the reagent in a cuvette were added 1 μl aliquots of serum standards or unknown. After mixing, 5 μl of an aqueous solution of the labeled conjugate prepared in part A (0.125 $A_{345}$ units per ml) was added to each cuvette and the rate of increase in fluorescence was monitored in each for 2 to 3 minutes. All solutions were kept at 25° C., except the labeled conjugate which was kept in an ice bath.

C. Results—Rate Assay

The absorbance spectrum of the labeled conjugate, β-galactosyl-umbelliferone-sisomicin, showed an absorbance maximum at 345 nm. When the conjugate was hydrolyzed with bacterial β-galactosidase to remove the galactose moiety, the absorbance at 345 nm decreased and a new maximum appeared at 402 nm. The absorbance of the enzyme-treated conjugate was 1.46 times that of the untreated conjugate.

Analysis of the fluorescence spectrum of the conjugate revealed a similar shift in the maximum wavelength. Before enzyme treatment, the conjugate exhibited excitation and emission maxima at 350 and 394 nm, respectively. After hydrolysis with β-galactosidase, a 15-fold increase in fluorescense was observed, with new excitation and emission maxima of 409 and 445 nm, respectively. Hence, under the conditions of the fluorescent assay (excitation and emission wavelengths of 400 and 453) the unreacted conjugate contributed negligible fluorescence. For all of the aminoglycoside antibiotic assays reported herein, the excitation and emission wavelengths used in the fluorometric measurements were approximately 400 and 450 nm, respectively.

The effect of antiserum to gentamicin on the ability of the labeled conjugate to function as a substrate for $\beta$-galactosidase was examined. Various amounts of antiserum were added to 2.0 ml of buffered $\beta$-galactosidase. The labeled conjugate was added and the reaction rate determined using an Aminco-Bowman Spectrofluorometer connected to a strip-chart recorder. Reaction rates are expressed in terms of recorder units/minute. As the amount of antiserum increased, the reaction rate decreased as shown in FIG. 2 of the drawings. Based upon this experiment, an amount of antiserum sufficient to inhibit the reaction rate by 70 to 80% was chosen for the competitive binding reactions. The reaction between the antibody and the conjugate appeared to be complete in the time required for mixing the reagents, because incubation of the conjugate with the antibody before adding enzyme did not alter the results.

For the standard curve, gentamicin standards were prepared from 0 to 14 $\mu$g/ml (mg/liter) in normal human serum and assayed as described in part B above. FIG. 3 of the drawings shows the standard curve of the reaction rate related to gentamicin concentration in serum standards. Reaction rate was calculated for each standard as the percentage of the maximum reaction rate in the absence of antiserum, after substraction of fluorescence in the absence of drug in the standard. No difference was observed for standards prepared in buffer compared to standards prepared in serum. Varying the time of incubation of the standards with the antibody/enzyme reagent from 0.25 to 60 minutes before adding the labeled conjugate did not alter the standard curve. Hence, the assay can be performed as rapidly as the reagents can be mixed.

D. Assay Procedure—Fixed-Time Assay

A reagent was prepared by adding 140 $\mu$l of antiserum to gentamicin (prepared as in part B above—to inhibit the maximum reaction rate in the final reagent by 75%) to 40 milliliter (ml) of 0.05 M Bicine buffer, pH 8.2. To 2.0 ml aliquots of this reagent in a cuvette were added 7.5 $\mu$l aliquots of serum standards. After mixing, 40 $\mu$l of an aqueous solution of the labeled conjugate prepared in part A (0.013 $A_{345}$ units per ml) were added to each cuvette. After further mixing, 30 $\mu$l of $\beta$-galactosidase solution (21 U/$\mu$l) were added to each cuvette and the solutions again mixed. After 20 minutes at room temperature, the resulting fluorescence for each cuvette was measured in the fluorometer and expressed in terms of the instrument reading.

E. Results—Fixed-Time Assay

Figure 4:
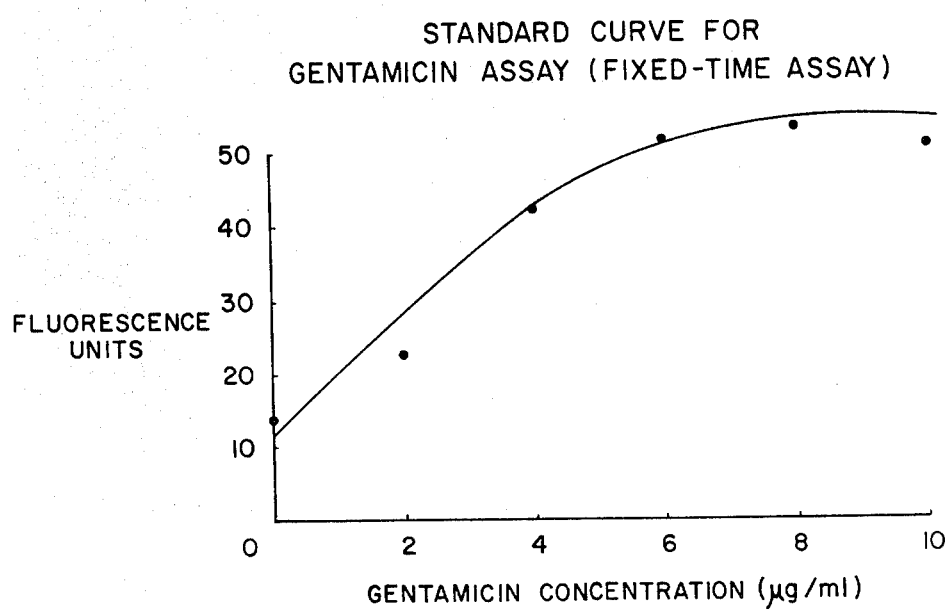
FIGS. 4-15 are graphical representations of the relations between the concentration of the various ligands listed below and fluorescence intensity or reaction rate as determined using standards according to Examples 1-7 and 9-14, respectively, for use as standard curves in assays for the various ligands.

A standard curve generated by testing various standard samples containing known concentrations of gentamicin according to the preceding method is depicted in FIG. 4 of the drawings.

EXAMPLE 2

Sisomicin Assay

A. Preparation of glycone-dye-drug conjugate

The labeled conjugate used in this Example was that prepared according to part A of Example 1.

B. Assay Procedure

A reagent was prepared by adding 170 $\mu$l of antiserum to gentamicin (prepared as in part B of Example 1—to inhibit the maximum reaction rate in the final reagent by 90%) and 150 $\mu$l of 0.1 mg/ml $\beta$-galactosidase (6 U) to 200 ml of 50 mM Bicine buffer. To 2.0 ml aliquots of this reagent in a cuvette were added 20 $\mu$l aliquots of aqueous standard sisomicin solutions. After mixing, 20 $\mu$l of an aqueous solution of the labeled conjugate (part A above—0.032 $A_{345}$ units per ml) were added to each cuvette. Fluorescence was measured in an Aminco-Bowman Spectrofluorometer and reaction rates calculated for each standard as in part C of Example 1.

C. Results

Figure 5:
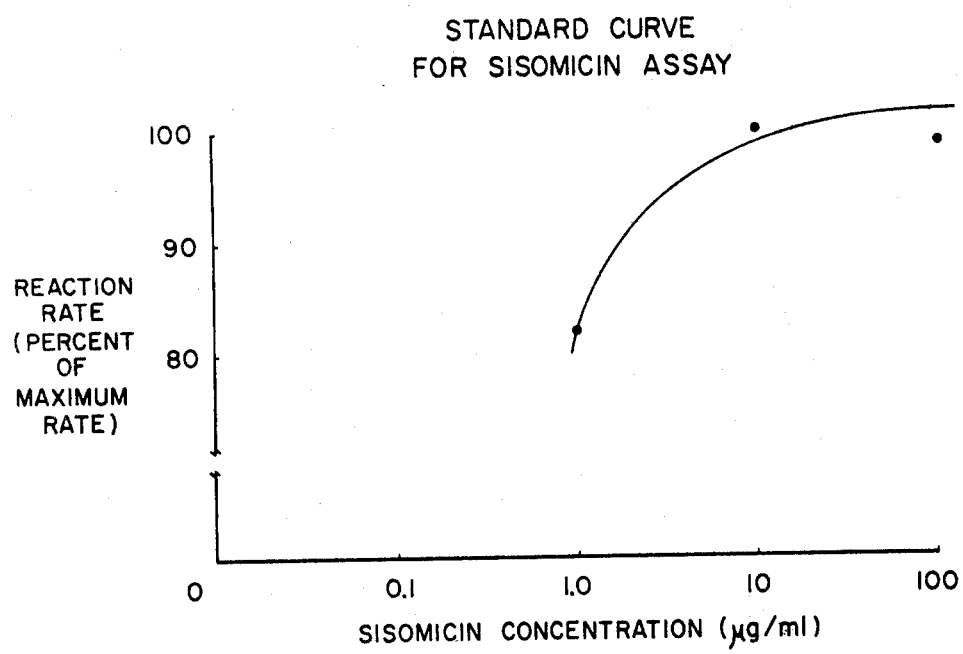

A standard curve generated by testing various standard samples of sisomicin according to the preceding method is depicted in FIG. 5 of the drawings.

EXAMPLE 3

Netilmicin Assay

A. Preparation of glycone-dye-drug conjugate

The labeled conjugate used in this Example was that prepared according to part A of Example 1.

B. Assay Procedure

The procedure was the same as that described in part B of Example 2 using aqueous netilmicin standards.

C. Results

Figure 6:
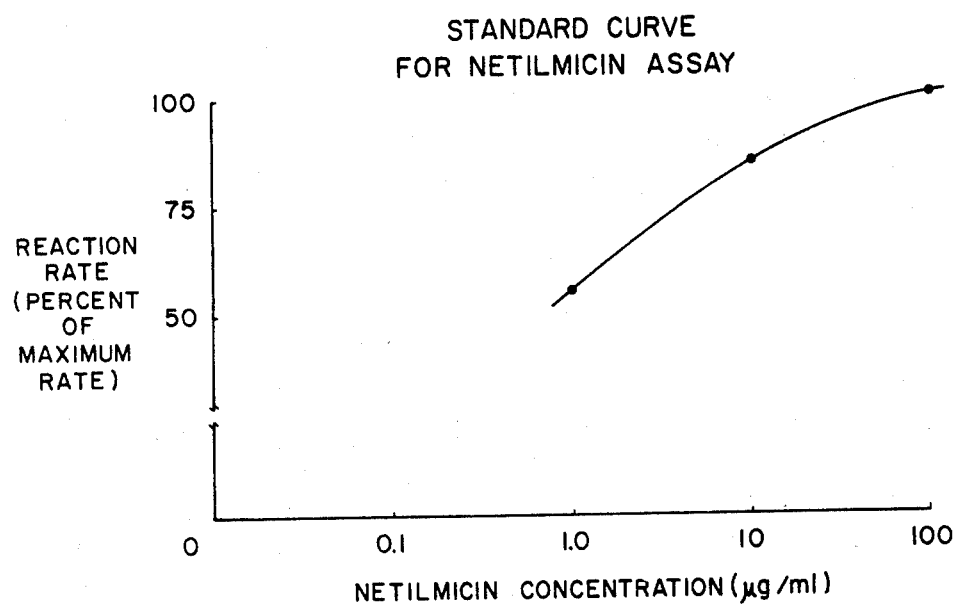

A standard curve generated for the assay of netilmicin according to the above procedure is depicted in FIG. 6 of the drawings.

EXAMPLE 4

Tobramycin Assay

A. Preparation of glycone-dye-drug conjugate

The reaction sequence and methodology for the preparation of the labeled tobramycin conjugate were basically those of Table 3 and part A of Example 1, respectively.

With 55 mg (135 $\mu$mol) of the potassium salt of 7-$\beta$-galactosylcoumarin-3-carboxylic acid was mixed 150 mg (220 $\mu$mol) of tobramycin (Eli Lilly & Co., Indianapolis, Ind. U.S.A.) in 1.5 ml of distilled water. The pH was adjusted to 3.65 by the dropwise addition of 1 N hydrochloric acid and the resulting solution cooled in an ice bath. To initiate the coupling reaction, 30 mg (160 $\mu$mol) of 1-ethyl-3(3-dimethylaminopropyl) carbodiimide hydrochloride were added. After overnight incubation of 4° C., two drops of 1 N sodium hydroxide were added to give a pH of 6.1.

The product was purified by chromatography on carboxymethyl Sephadex gel (Pharmacia Laboratories, Inc.) with ammonium formate as eluant. After an initial wash with 0.05 M ammonium formate to remove unreacted galactoside, 1.5 M ammonium formate was used to elute conjugated products. Five peaks of material absorbing at 345 nm were eluted, with the third peak being selected for use in this study.

B. Assay Procedure

A reagent was prepared by adding 150 $\mu$l of antiserum to tobramycin (prepared as described in part B of Example 1 using tobramycin in place of gentamicin in synthesis of the immunogen—to inhibit the maximum reaction rate in the final reagent by 80%) and 250 $\mu$l of an aqueous solution of $\beta$-galactosidase (4 U/ml) to 100 ml of 0.05 M Bicine buffer, pH 8.2. To 2.0 ml aliquots of this reagent in a cuvette were added 10 $\mu$l aliquots of aqueous standard tobramycin solutions followed by 20 $\mu$l of an aqueous solution of the labeled conjugate prepared as in part A (0.03 $A_{345}$ units per ml). After measuring the rate of resulting fluorescence, reaction rates were calculated for each standard as in part C of Example 1.

C. Results

Figure 7:
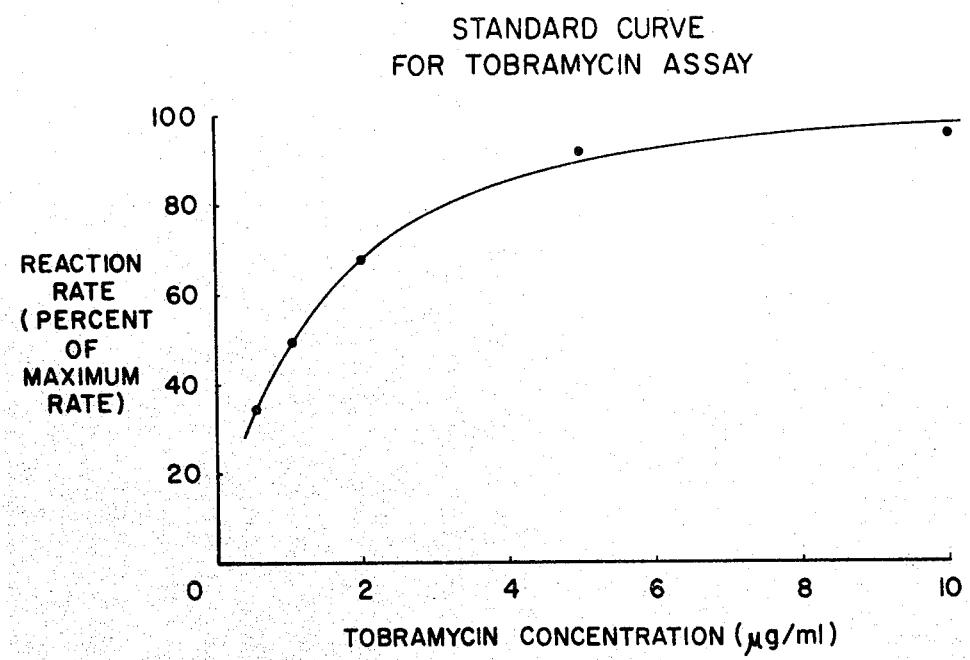

A standard curve generated by testing various tobramycin standard samples according to the preceding method is depicted in FIG. 7 of the drawings.

EXAMPLE 5

Kanamycin Assay

A. Preparation of glycone-dye-drug conjugate

The labeled conjugate used in this Example was that prepared according to part A of Example 4.

B. Assay Procedure

The procedure was the same as that described in part B of Example 4 using aqueous kanamycin standards.

C. Results

Figure 8:
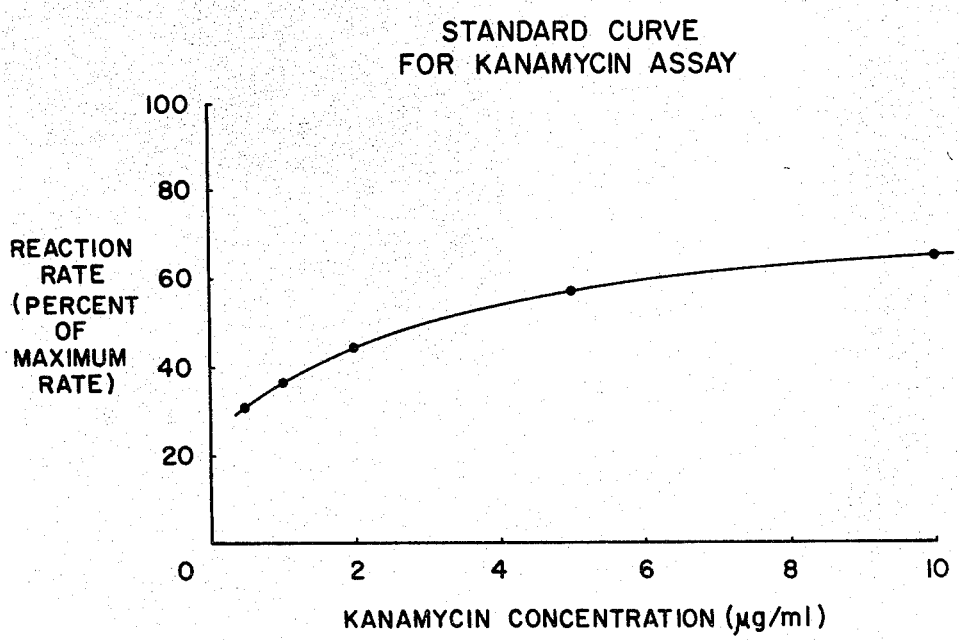

A standard curve generated for the assay of kanamycin according to the above procedure is depicted in FIG. 8 of the drawings.

EXAMPLE 6

Amikacin Assay

A. Preparation of glycone-dye-drug conjugate

The reaction sequence and methodology for the preparation of the labeled amikacin conjugate were basically those of Table 3 and part A of Example 1, respectively.

290 mg (540 μmol) of amikacin (Bristol Laboratories, Syracuse, N.Y. U.S.A.) were mixed 110 mg (270 μmol) of the potassium salt of 7-β-galactosylcoumarin-3-carboxylic acid in 3 ml of distilled water. The pH was adjusted to 4.1 by addition of 1 N hydrochloric acid. After the solution had been cooled in an ice bath, 55 mg (292 μmol) of 1-ethyl-3(3-dimethylaminopropyl) carbodiimide hydrochloride were added to initiate the reaction. After overnight incubation at 4° C., the reaction mixture was chromatographed on carboxymethyl Sephadex gel. After washing the column with 0.05 M ammonium formate to remove unreacted galactoside, 1.5 M ammonium formate was used to elute the desired conjugate. Three peaks of material absorbing at 345 nm were obtained, with the last peak being used for this study.

B. Assay Procedure

A reagent was prepared by adding 80 μl of antiserum to amikacin (prepared as described in part B of Example 1 using amikacin in place of gentamicin in synthesis of the immunogen to inhibit the maximum reaction rate in the final reagent by 70%) and 60 μl of an aqueous solution of β-galactosidase (4 U/ml) to 60 ml of 0.05 M Bicine buffer, pH 8.2. To 2.0 ml aliquots of this reagent in a cuvette were added 10 μl aliquots of aqueous amikacin standard solutions followed by 20 μl of an aqueous solution of the labeled conjugate prepared as in part A (0.03 $A_{345}$ units per ml). After measuring the rate of resulting fluorescence, reaction rates were calculated for each standard as in part C of Example 1.

C. Results

Figure 9:
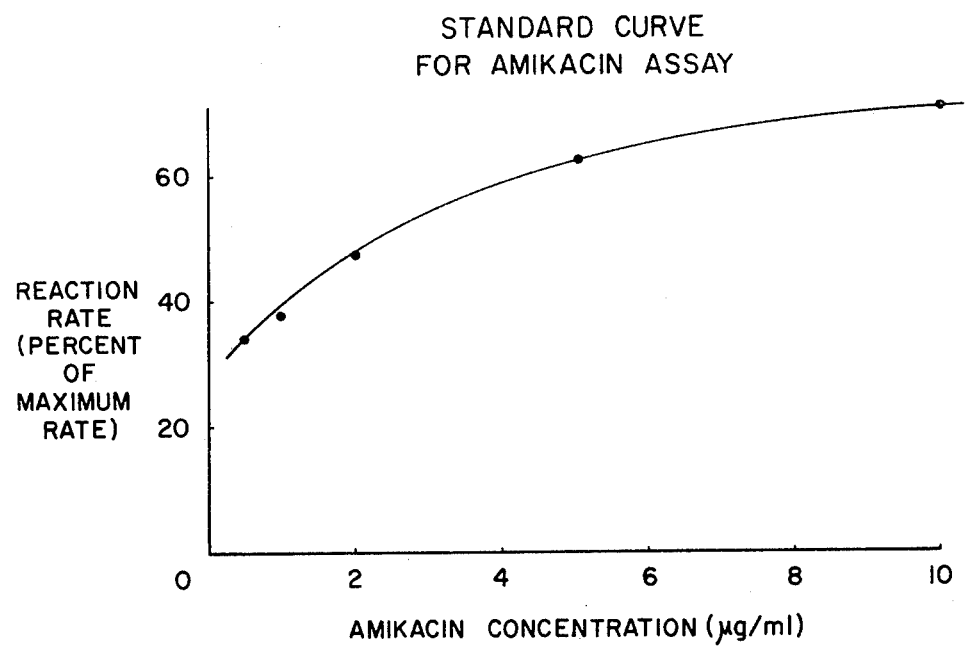

A standard curve generated by testing various amikacin standard samples according to the preceding method is depicted in FIG. 9 of the drawings.

EXAMPLE 7

Diphenylhydantoin Assay

Diphenylhydantoin [5,5-diphenyl-2,4-imidazolidinedione, cf. *The Merck Index*, 9th ed., p. 952(1976)], also known by the generic name phenytoin and sold under various trademarks including Dilantin, is an anti-convulsant drug useful in the management of epilepsy. In most patients, the therapeutic range of serum concentration lies between 10 and 20 μg/ml whereas toxic signs of nystagmus, ataxia, and mental changes almost invariably occur at blood levels over 20 μg/ml.

A. Preparation of glycone-dye-drug conjugate

In a liter, 3-neck round bottom flask was placed 8.64 g of a 50% suspension of sodium hydride (NaH) in mineral oil (0.18 mol). The NaH was washed free of mineral oil with hexane under an argon atmosphere. It was then suspended in 350 ml of dry dimethylformamide (DMF) and stirred while a solution of 34.4 g (0.173 mol) of N-(4-bromobutyl)phthalimide in 150 ml of dry DMF was added over a 20 minute period. After stirring at room temperature for 18 hours, the reaction was diluted with 200 ml of water and the precipitate collected and dried to yield 49 g of 2-[(4-N-phthalimido)-butoxy]benzophenone, mp 119°–121° C. A 1 g sample was recrystallized from ethanol to give 740 mg of white needles, mp 121°–122° C.

A mixture of 22.4 g (0.056 mol) of 2-[(4-N-phthalimido)butoxy]benzophenone, 4.15 g (0.064 mol) of potassium cyanide, 17.3 g (0.18 mol) of ammonium carbonate, 24 ml of water, and 200 ml of DMF was placed in a steel autoclave and heated at 110° C. for 4 days. The contents were cooled and adsorbed onto 100 g of silica gel 60 and placed atop a column of 700 g of silica gel made up in 9:1 (v:v) carbon tetrachloride:acetone. Elution was with the same solvent and fractions of approximately 20 ml volumes were collected. Fractions 276–803 were combined and evaporated to give 4.65 g of solid. Recrystallization from ethanol gave 2.65 of 5-[2-(4-N-formylamino)butoxyphenyl]-5-phenylhydantoin as a white solid, mp 201°–203° C.

A solution of 3.5 g (9.4 mmol) of 5-[2-(4-N-formylamino)butoxyphenyl]-5-phenylhydantoin in 100 ml of 1 N sodium hydroxide was heated on the steam bath for 24 hours. The solution was cooled and neutralized with carbon dioxide until precipitation ceased. The precipitate was filtered and recrystallized twice; first from pyridine-2-propanol, then from methanol to give 1.5 g of 5-[2-(4-aminobutoxy)phenyl]-4-phenylhydantoin as fine white crystals, mp 235° C. (decomp).

A mixture of 808 mg (2 mmol) of the potassium salt of 7-β-galactosylcoumarin-3-carboxylic acid [Burd et al, *Clin. Chem.* 23:1402 (1977)] and 20 ml of dry DMF was made and cooled to 0° C. To this mixture was added 216 mg (2 mmol) of ethylchloroformate. After stirring for one hour at this temperature, 638 mg (2 mmol) of 5-[2-(4-aminobutoxy)phenol]-5-phenylhydantoin, 244 mg of 4-dimethylaminopyridine, and 5 ml of dry pyridine were added. After stirring for 5 hours, the reaction was stored overnight at 0° C., then adsorbed onto 7 g of silica gel 60. The impregnated silica gel was placed atop a column of 200 g of silica gel 60 and the column eluted with a gradient of 2 liters of ethyl acetate to 2 liters of 1:1 (v:v) ethyl acetate:ethanol. Ten ml fractions were collected. Fractions 143–160 were combined to give approximately 200 mg of the labeled conjugate N-{4-[2-(5-phenylhydantoinyl-5)phenoxy]butyl}-7-β-galactosylcoumarin-3-carboxamide as a glassy solid.

The solid was taken up in methanol and chromatographed on Sephadex LH-20 (45 cm by 3.2 cm), eluting with methanol. Seven ml fractions were collected. Fractions 30 to 40 were combined and evaporated to give 100 mg of the desired labeled conjugate as a pale, glossy solid.

Analysis: Calculated for $C_{35}H_{35}N_3O_{12} \cdot H_2O$: C, 59.40; H, 5.24; N, 4.95. Found: C, 59.51; H, 5.04; N, 6.14. $[\alpha]_D = -39.04°$ (c 1.0, methanol).

B. Assay Procedure

A reagent was prepared containing β-galactosidase (0.018 U/ml) and antiserum to diphenylhydantoin (raised against o-caproyldiphenylhydantoin—in an amount sufficient in the final reagent to decrease fluorescence to 10% of that observed in the absence of antibody) in 50 mmolar Bicine buffer, pH 8.2. To 3.0 ml aliquots of this reagent in a cuvette were added 100 μl aliquots of the labeled conjugate (part A above). After mixing, the reaction mixtures were incubated 20 minutes at room temperature and fluorescence measured in each cuvette (excitation and emission wavelengths were 400 and 450 nm, respectively).

C. Results

Figure 10:
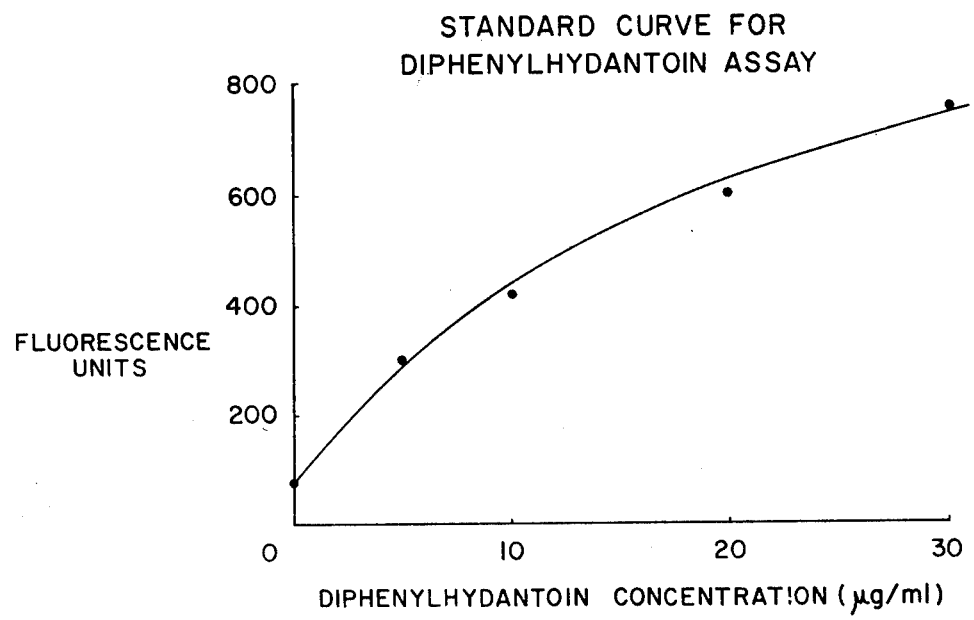

A standard curve generated for the assay of diphenylhydantoin according to the above procedure is depicted in FIG. 10 of the drawings.

EXAMPLE 8

Fixed-Time Assays for the Aminoglycoside Antibiotics

A. Reagents

1. Buffer—Bicine buffer [N,N-bis-(2-hydroxyethyl)-glycine from Calbiochem, La Jolla, Calif.] was used at 50 mM, pH 8.5, at 25° C.

2. Enzyme—*E. coli* grade IV β-galactosidase was used (Worthington Biochemicals, Co., Freehold, N.J.). One unit of enzyme hydrolyzes 1.0 μmol of o-nitrophenyl-β-D-galactoside per minute when assayed at 25° C. in 50 mM Bicine buffer with 0.1% $NaN_3$, pH 8.5, containing 3 mM o-nitrophenyl-β-D-galactoside.

3. Antiserum, Standards and Fluorogenic Reagent—These are listed in the Reagent Table below as used for the fixed-time assay of the indicated aminoglycoside antibiotics. The fluorogenic Reagents consisted of a solution prepared in 5 mM formate—0.1% sodium azide buffer, pH 3.5, which contained 0.007 $A_{343}$ units of the respective labeled conjugate.

B. Fixed-Time Assay Procedure

A reagent was prepared in 50 mM Bicine buffer, pH 8.5, which contained 0.05 units of β-galactosidase per ml and an amount of antiserum sufficient to decrease the enzyme reaction to about 30% of that observed in the absence of an antiserum. To 3.0 ml of this reagent in individual cuvettes was added 100 μl of a standard which had been previously diluted 1 part to 50 parts of buffer. At 30 second intervals, 100 μl of the Fluorogenic Reagent was added to the cuvettes and the contents mixed by gentle inversion of the cuvettes. At 20 minutes after addition of the Fluorogenic Reagent, the fluorescence intensity in the individual cuvettes was measured with an Aminco-Bowman Spectrophotofluorometer (American Instrument Co., Silver Spring, Md.) using 400 nm for excitation and 450 nm for emission. All fluorescence measurements were conducted at 25° C.

REAGENT TABLE

| Ligand Under Assay | Immunogen used to raise Antiserum[1] | Ligand used to prepare Standards | Fluorogenic Reagent |
|---|---|---|---|
| Gentamicin | Gentamicin | USP Gentamicin | βGU[2]-sisomicin (Ex. 1, Part A) |
| Sisomicin | Gentamicin | Sisomicin sulfate[3] | βGU[2]-sisomicin (Ex. 1, Part A) |
| Netilmicin | Gentamicin | Netilmicin Standards[4] | βGU[2]-sisomicin (Ex. 1, Part A) |
| Tobramycin | Kanamycin | USP Tobramycin | βGU-tobramycin (Ex. 4, Part A) |
| Kanamycin | Kanamycin | Kanamycin sulfate[5] | βGU-tobramycin (Ex. 4, Part A) |
| Amikacin | Amikacin | Amikacin[5] | βGU-amikacin (Ex. 6, Part A) |

[1] raised in rabbits against BSA-antibiotic conjugate
[2] β-galactosyl-umbelliferone
[3] from Schering Corp., Bloomfield, New Jersey
[4] purchased from Monitor Science Corp. Newport Beach, California
[5] from Bristol Laboratories, Syracuse, New York C. Results For each respective aminoglycoside antibiotic assay, the cuvette containing the highest standard was used to set the fluorescence meter to a predetermined reading as indicated in the Results Table below. Further readings were then made without adjusting the fluorometer. The results are given in the Results Table below.

RESULTS TABLE

| Ligand Under Assay | Concentration of Standard (μg/ml) | Fluorescence Intensity (Arbitrary Units) |
|---|---|---|
| Gentamicin | 12 | 93.5 |
|  | 8 | 78.5 |
|  | 4 | 54.5 |
|  | 1 | 34.5 |
| Sisomicin | 20 | 90.0 |
|  | 14 | 77.3 |
|  | 10 | 71.0 |
|  | 6 | 47.3 |
|  | 2 | 24.0 |
|  | 0 | 19.3 |
| Netilmicin | 16 | 74.8 |
|  | 8 | 62.8 |
|  | 4 | 47.0 |
|  | 2 | 36.5 |
|  | 1 | 33.2 |
| Tobramycin | 12 | 81.7 |
|  | 8 | 66.3 |
|  | 4 | 48.7 |
|  | 1 | 37.3 |
| Kanamycin | 40 | 87.7 |
|  | 25 | 71.5 |
|  | 10 | 47.8 |
|  | 5 | 39.5 |
|  | 0 | 32.0 |
| Amikacin | 40 | 90.0 |
|  | 30 | 81.5 |
|  | 20 | 66.0 |
|  | 10 | 47.5 |
|  | 0 | 33.5 |

EXAMPLE 9

Phenobarbital Assay

Phenobarbital [5-ethyl-5-phenylbarbituric acid, cf. *The Merck Index*, 9th ed., p. 939(1976)], sold under various trademarks including Luminal, is an anticonvulsant drug useful in the management of epilepsy. In most patients, the therapeutic range of serum concentration lies between 15 and 40 μg/ml whereas toxicity almost invariably appears at blood levels over 50 μg/ml.

A. Preparation of glycone-dye-drug conjugate

β-galactosyl-umbelliferone labeled phenobarbital conjugates are prepared according to the reaction scheme shown in Table B in the drawings. This synthetic route is exemplified by the following method of preparing 5-[4-(7-β-galactosylcoumarin-3-carboxamido)butyl]-5-phenylbarbituric acid (6), n=4.

Diethyl 2-Carbethoxy-2-phenylpimelate (1)

A 50% mineral oil dispersion of 2.4 g (0.1 mol) of sodium hydride was placed in a 500 ml, 3-neck round bottom flask under an argon atmosphere. It was washed free of oil with 250 ml of dry hexane and combined with 23.6 g (0.1 mol) of diethyl phenylmalonate (Aldrich Chemical Co., Milwaukee, WI) dissolved in 100 ml of dry dimethylformamide (DMF). The mixture was stirred at room temperature for 15 minutes, during which time hydrogen evolution ceased. A solution of 20.9 g (0.1 mol) of ethyl 5-bromopentanoate (Aldrich Chemical Co., Milwaukee, WI) in 100 ml of dry DMF was added and the reaction stirred overnight at 70° C. Removal of the DMF on a rotary evaporator at 50° C./0.3 mm left an oily residue that was partitioned between 300 ml of water and 500 ml of ethyl acetate. The organic phase was separated, washed with 500 ml of water, 200 ml of saturated sodium chloride solution, and dried over anhydrous magnesium sulfate. It was filtered and evaporated to give an oil that was chromatographed on 1500 g of silica gel (E. Merck Co., Darmstadt, West Germany). The column was eluted with chloroform and 20 ml fractions were collected.

Fractions 771 to 1200 were combined and evaporated to give an oil that was evaporatively distilled at 160° C./0.01 mm to yield 28 g (77% yield) of the desired product (1) as a white oil.

Analysis: Calculated for $C_{20}H_{28}O_6$: C, 65.91; H, 7.74. Found: C, 65.90; H, 7.75. Infrared Spectrum (neat): 1735 cm$^{-1}$ (carbonyl).

5-(4-Carbethoxybutyl)-5-phenyl-2-thiobarbituric Acid (2) and 5-(4-Carboxybutyl)-5-phenylbarbituric Acid (3).

A solution of 3.68 g (0.16 g-atm) of sodium and 15.2 g (0.2 mol) of thiourea in 100 ml of ethanol was refluxed while stirring under an argon atmosphere. To this was added, dropwise over 30 minutes, 28 g (0.08 mol) of diethyl 2-carbethoxy-2-phenylpimelate (1). After refluxing for 6 hours, the reaction was cooled and concentrated on a rotary evaporator. The residue was taken up in 200 ml of water and extracted with 200 ml of ethyl acetate followed by 200 ml of ether. The aqueous phase was acidified to pH 1 which caused the precipitation of a heavy yellow oil. This oil was chromatographed on 850 g of silica gel. The column was eluted with 9:1 (v:v) toluene: ethanol and 20 ml fractions were collected.

Fractions 45 to 63 were combined, evaporated to dryness, and the solid residue recrystallized from aqueous ethanol. This gave 5 g (18% yield) of the thiobarbituric acid (2) as pale yellow crystals, mp 121° C.

Analysis: Calculated for $C_{17}H_{26}N_2SO_4$: C, 58.60; H, 5.79; N, 8.04. Found: C, 58,42; H, 5.82; N, 8.07.

Infrared Spectrum (KCl): 1735 cm$^{-1}$ (carbonyl); 1675 cm$^{-1}$ (carbonyl).

Fractions 64 to 100 were combined and evaporated to give 6 g of slightly impure (2). This was taken up in 50 ml of dimethyl sulfoxide containing 1 ml of concentrated sulfuric acid and heated on the steam bath for 3 hours. [Mikolajczyk and Luczak, *Chem. Ind.* 77 (1972)]. When cool, the dimethyl sulfoxide was removed under high vacuum. To the residue was added 25 ml water and 25 ml of dioxane and the solution heated on the steam bath for 2 hours. Removal of the solvent gave a dark residue that was partitioned between 200 ml of ether and 200 ml of aqueous sodium bicarbonate solution. The aqueous phase was filtered and neutralized with hydrochloric acid. A solid precipitated that was recrystallized from aqueous ethanol to give 1.9 g (36% yield) of the barbituric acid (3) as white crystals, mp 202°–203° C.

Analysis: Calculated for $C_{15}H_{16}N_2O_5$: C, 59.20; H, 5.30; N, 9.21. Found: C, 58.65; H, 5.34; N, 9.25.

NMR Spectrum ($C_5D_5N$): δ 1.9 (m, 4H); δ 2.6 (m, 4H); δ 7.3 (m, 3H); δ 7.8 (m, 2H).

5-(4-Aminobutyl)-5-phenylbarbituric Acid (4).

A mixture of 15 ml of concentrated sulfuric acid, 7 g (0.023 mol) of barbituric acid (3) and 3.45 g (0.053 mol) of sodium azide was placed in a small, stainless steel stirring autoclave and heated to 60° C. After 90 minutes the autoclave was cooled, opened, and the black suspension rinsed out with 300 ml of water and neutralized with solid sodium bicarbonate. It was combined with 50 g of celite (Fischer Scientific Co., Pittsburgh, PA) and the water removed on a rotary evaporator. This left a dirty gray mass that was air dried, then ground to a fine consistency in a mortar. It was placed atop a 250 g column of silica gel made up in 9:1 (v:v) ethanol: 1 M aqueous triethylammonium bicarbonate. The column was eluted with this solvent and 20 ml fractions were collected.

Fractions 73 to 107 were combined and evaporated to give a solid residue. It was taken up in dilute hydrochloric acid, evaporated to dryness, and this residue recrystallized from ethanol to give 1.75 g (24% yield) of the hydrochloride salt of 5-(4-aminobutyl)-5-phenylbarbituric acid (4) as fine white needles that did not melt below 280° C.

Analysis: Calculated for $C_{14}H_{17}N_3O_3.HCl$: C, 53.93; H, 5.82; N, 13.48. Found: C, 53.44; H, 5.94; N, 13.29.

Infrared Spectrum (KCl): 1710 cm$^{-1}$ (carbonyl).

5-[4-(7-β-Galactosylcoumarin-3-carboxamido)butyl]-5-phenylbarbituric Acid (6)

A mixture of 737 mg (2 mmol) of 7-β-galactosylcoumarin-3-carboxylic acid [Burd et al, *Clin. Chem.* 23:1402(1977)], 0.278 ml (202 mg, 2 mmol) of triethylamine, and 25 ml of dimethylformamide was cooled to −5° C. in a methanol-ice bath while stirring under an argon atmosphere. To this was added 273 mg (2 mmol) of isobutyl chloroformate. After 1 hour at this temperature a precipitate of triethylamine was present, indicating conversion to the mixed anhydride (5). At this point, 551 mg (2 mmol) of the amine (4) was added. The reaction was stirred at −5° C. for 2 hours, then allowed to warm to room temperature overnight. Eight grams of silica gel was added and the solvent removed on a rotary evaporator under high vacuum. The impregnated silica gel was placed atop a column of 200 g of silica gel made up in ethyl acetate. The column was eluted with a gradient of 2 L of ethyl acetate to 2 L of 1:1 (v:v) ethyl acetate: ethanol and 15 ml fractions were collected.

Fractions 126 to 175 were combined and evaporated to give 750 mg (80% yield) of the desired conjugate (6) as a white solid, mp 161°–163° C.

Analysis: Calculated for $C_{30}H_{31}N_3O_{12}$: C, 57.60; H, 4.99; N, 6.72. Found: C, 57,54; H, 5.29; N, 6.27.

Infrared Spectrum (KCl): 1710 cm$^{-1}$ (carbonyl).

Optical Rotation: $[\alpha]_D = -45.58°$ (c 1.0, $CH_3OH$).

Mass Spectrum (field desorption): m/e 626 [P+1].

The above-described synthesis of the β-galactosyl-coumarin-phenobarbital conjugate (6) (n=4) can be modified to yield labeled conjugates wherein n=2 through 6 by replacing the starting material ethyl 5-bromopentanoate with the appropriate ethyl ω-bromoalkanoate as follows:

| n | alkylene |
|---|----------|
| 2 | ethylene |
| 3 | propylene |
| 5 | pentylene |
| 6 | hexylene |

B. Assay Reagents

1. Antiserum—Antiserum was collected from rabbits which were immunized with a phenobarbital-bovine serum albumin immunogen conjugate.

2. Enzyme—*E. coli* grade IV β-galactosidase was used (Worthington Biochemicals, Co., Freehold, NJ). One unit of enzyme hydrolyzes 1.0 μmole of o-nitrophenyl-β-D-galactoside per minute when assayed at 25° C. in 50 mM Bicine buffer [N,N-bis-(2-hydroxyethyl)-glycine from Calbiochem, La Jolla, CA], pH 8.5, containing 3 mM o-nitrophenyl-β-D-galactoside.

3. Buffer—Bicine buffer was used at 50 mmolar, pH 8.5, at 25° C.

4. Phenobarbital standards were prepared from USP primary standard materials.

5. Fluorogenic Phenobarbital Reagent—A solution was prepared in 5 mM formate—0.1% azide buffer, pH 3.5, which contained 0.016 absorbance units at 343 nm ($A_{343}$) of β-galactosyl-umbelliferone-phenobarbital (Part A).

C. Assay Procedure

A reagent was prepared in 50 mM Bicine buffer, pH 8.5, which contained 0.05 units of β-galactosidase per ml and an amount of antiserum sufficient to decrease the enzyme reaction to about 15% of that observed in the absence of antiserum. To 3.0 ml of this reagent in individual cuvettes was added 100 μl of phenobarbital standards which had previously been diluted 1 part to 50 parts of buffer. At 30 second intervals, 100 μl of the Fluorogenic Phenobarbital Reagent was added to the cuvettes and the contents mixed by gentle inversion of the cuvettes. At 20 minutes after addition of the Fluorogenic Phenobarbital Reagent, the fluorescence intensity in the individual cuvettes was measured with an Aminco-Bowman Spectrophotofluorometer (American Instrument Co., Silver Spring, Md). Excitation and emission wavelengths were set at 400 and 450 nm, respectively. All fluorescence measurements were conducted at 25° C.

D. Results

Figure 11:
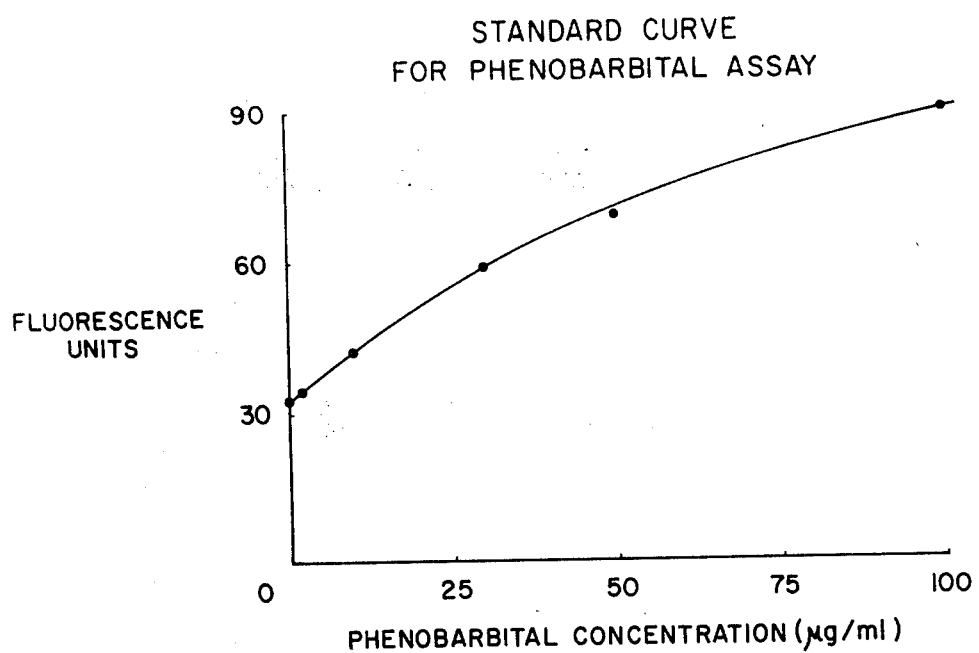

The cuvette containing the highest phenobarbital standard was used to set the fluorescence meter to a reading of 90 units. Further readings were then made without adjusting the fluorometer. A standard curve generated by the assay of phenobarbital according to the above procedure is depicted in FIG. 11 of the drawings.

EXAMPLE 10

Theophylline Assay

Theophylline [1,3-dimethylxanthine, cf. *The Merck Index*, 9th ed., p. 1196(1976)] is a drug useful in the management of asthma. In most patients, the therapeutic range of serum concentration lies between 10 and 20 μg/ml whereas toxicity almost invariably appears at blood levels over 35 μg/ml.

A. Preparation of glycone-dye-drug conjugate

β-galactosyl-umbelliferone-labeled theophylline conjugates are prepared according to the reaction scheme shown in Table C in the drawings. This synthetic route is exemplified by the following method of preparing 8-[3-(7-β-galactosylcoumarin-3-carboxamido)propyl]-theophylline (10), n=3.

8-(3-Aminopropyl)theophylline (8)

A mixture of 2.66 g (0.01 mol) of 8-(3-carboxypropyl)theophylline (7) [Cook et al, *Res. Commun. Chem. Path. Pharmacol.* 13(3):497–505(1976)], 20 ml of chloroform, and 3 ml of concentrated sulfuric acid was stirred at 50° C. under an argon atmosphere. To this was added 1.3 g of solid sodium azide portionwise over a 90 minute period [cf. *Organic Reactions* 47:28(1967)]. The reaction was cooled and the solvent removed under reduced pressure. The residue was combined with enough sodium bicarbonate solution to bring the pH to 7.5. Ten grams of celite (Fisher Scientific Co., Pittsburgh, PA) was added and the water evaporated. The impregnated celite was placed atop a column of 200 g of silica gel (E. Merck Co., Darmstadt, West Germany) made up in 9:1 (v:v) ethanol—1 molar aqueous triethylammonium bicarbonate. The column was eluted with this solvent and 15 ml fractions were collected. Fractions 171 to 225 were combined and evaporated to give 500 mg of a white powder. This substance was rechromatographed on a column of CM-Sephadex, ammonium form (Pharmacia Fine Chemicals, Piscataway, NJ), eluting with 0.5 molar ammonium bicarbonate. The bed volume was 3 cm by 50 cm; and 10 ml fractions were collected. Fractions 65 to 110 were combined and evaporated to give 250 mg of a white solid. It was taken up in dilute hydrochloric acid, then reevaporated.

The residue was recrystallized from methanol to give 90 mg (3% yield) of the hydrochloric acid salt of (8) as pale tan needles that did not melt below 300° C.

Analysis: Calculated for $C_{10}H_{16}N_5ClO_2$: C, 43.88; H, 5.89; N, 25.59. Found: C, 43.77; H, 5.88; N, 25.46.

Infrared Spectrum (KCl): 1695 cm$^{-1}$ and 1655 cm$^{-1}$ (amide carbonyls).

8-[3-(7-β-Galactosylcoumarin-3-carboxamido)propyl]-theophylline (10).

A reaction mixture was prepared containing 24 g of potassium hydroxide, 80 ml of water, 240 ml of methanol, and 20 g (0.035 mmol) of ethyl 7-β-galactosyl-coumarin-3-carboxylate [Burd et al, *Clin. Chem.* 23:1402 (1977)]. The reaction was stirred at 50° C. for 15 hours. When cool, the methanol was removed under reduced pressure. The concentrated aqueous solution was acidified to pH 2.0 with concentrated hydrochloric acid. The white precipitate was collected, washed with cold water, and recrystallized from hot water. The crystals were collected, washed with acetone, and dried at 80° C. for 1 hour. This gave 12 g of 7-β-galactosylcoumarin-3-carboxylic acid as white crystals, mp 250°–255° C.

A mixture of 1.45 g (0.004 mol) of 7-β-galactosylcoumarin-3-carboxylic acid, 404 mg (0.004 mol) of triethylamine, and 40 ml of dry dimethyl formamide (DMF) was cooled to $-10°$ C. while stirring under argon. To this was added 546 mg (0.004 mol) of isobutyl chloroformate (Aldrich Chemical Co., Milwaukee, WI) to form the mixed anhydride (9). Ten minutes later, an additional 404 mg of triethylamine and 949 mg (0.004 mol) of 8-(3-aminopropyl)theophylline (8) was added to the flask. After stirring for 30 minutes at $-10°$ C., the reaction was allowed to warm to room temperature. It was combined with 10 g of silica gel and the DMF removed under high vacuum. The impregnated silica gel was placed atop a column of 170 g of silica gel and the column eluted with anhydrous ethanol and collecting 15 ml fractions. Fractions 41 to 475 were combined and evaporated to give 545 mg of a yellow solid. It was dissolved in water, filtered, and concentrated to a 20 ml volume. A small amount of precipitate formed and was discarded. The filtrate was chromatographed on a 2.5 cm by 57 cm column of Sephadex LH-20 gel (Pharmacia Fine Chemicals, Piscataway, NJ), eluting with water and collecting 15 ml fractions. Fractions 18 to 23 were combined, evaporated, and the residue recrystallized from water to give 55 mg (2% yield) of the labeled conjugate (10) as a light yellow solid, mp 190°–192° C.

Analysis: Calculated for $C_{26}H_{29}N_5O_{11}$: C, 53.15; H, 4.98; N, 11.92. Found: C, 52.65; H, 5.01; N, 11.80.

The above-described synthesis of the β-galactosyl-coumarin-theophylline conjugate (10), n=3, can be modified to yield labeled conjugates wherein n=2 through 6 by replacing the starting material 8-(3-carboxypropyl)theophylline (7), n=3, with the appropriate 8-(ω-carboxyalkyl)theophylline as follows:

| n | alkylene |
|---|---|
| 2 | ethylene |
| 4 | butylene |
| 5 | pentylene |
| 6 | hexylene |

B. Assay Reagents

1. Antiserum—Antiserum was collected from rabbits immunized with a theophylline immunogen conjugate prepared as described by Cook et al, *Res. Comm. Chem. Path. Pharmacol.* 13:497–505(1976).

2. Enzyme and Buffer—Same as those described in Parts B-2 and B-3 in Example 9.

3. Theophylline standards were prepared from USP theophylline reference standard and normal human serum containing from 0 to 40 μg/ml of theophylline.

4. Fluorogenic Theophylline Reagent—A solution was prepared in 5 mM formate—0.1% sodium azide buffer, pH 3.5, which contained 0.01 $A_{348}$ units (12.3 mM) of the labeled conjugate (Part A).

C. Assay Procedure and Results

Figure 12:
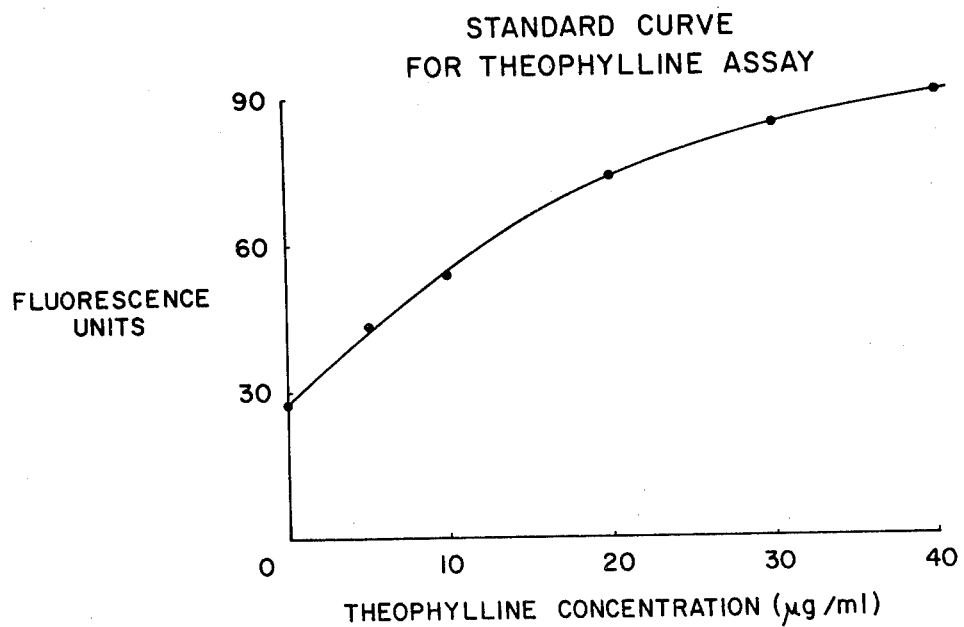

The procedure was the same as in Example 9 using theophylline standards and Fluorogenic Theophylline Reagent in place of the phenobarbital reagents. A standard curve generated for the assay of theophylline according to this procedure is depicted in FIG. 12 of the drawings.

EXAMPLE 11

Carbamazepine Assay

Carbamazepine [5H-dibenz[b,f]azepine-5-carboxamide, cf. *The Merck Index*, 9th ed., p. 226(1976)], sold under various trademarks including Tegretol, is an anticonvulsant drug useful in the mangagement of epilepsy. The therapeutic range of serum concentration in most patients lies between 4 and 12 μg/ml whereas toxic signs may appear at blood levels over 12 μg/ml.

A. Preparation of glycone-dye-drug conjugate

β-galactosyl-umbelliferone-labeled carbamazepine conjugates are prepared according to the reaction scheme shown in Table D in the drawings. This synthetic route is exemplified by the following method of preparing N-[4-(7-β-galactosylcoumarin-3-carboxamido)butyl]aminocarbonyl-5H-dibenz[b,f]azepine (14), n=4.

N-(4-Aminobutyl)aminocarbonyl-5H-dibenz[b,f]azepine (12).

Phosgene gas was bubbled into a room temperature suspension of 14.1 g (0.073 mol) of 5H-dibenz[b,f]azepine (Aldrich Chemical Co., Milwaukee, WI) in 180 ml of dry toluene until 15 g was absorbed. The warm mixture was stirred for 2 hours, heated at reflux for 2 hours, then stirred at room temperature overnight. The yellow solution, now containing N-chlorocarbonyl-5H-dibenz[b,f]azepine (11), was concentrated by boiling to about 100 ml volume. It was added dropwise over 1 hour to a solution at room temperature of 26 g (0.29 mol) of 1,4-diaminobutane in 250 ml of toluene. A white crystalline solid began to precipitate immediately. After the addition was complete, the resulting slurry was stirred at reflux for 3 hours. It was then cooled, filtered, and the precipitate washed with toluene. The filtrate was evaporated and excess butane diamine was removed by heating to 100° C. at 0.2 mm. The residual oil was taken up in dilute hydrochloric acid and some insoluble material filtered off. The solution was made basic to pH 9.5 with sodium carbonate and extracted with chloroform. Evaporation of this extract gave a glass that solidified when triturated with ether. This gave 15.8 g (70% yield) of the amine (12), as a solid, mp 114°–116° C.

Analysis: Calculated for $C_{19}H_{21}N_3O$: C, 74.24; H, 6.89; N, 13.67. Found: C, 73.92; H, 6.71; N, 13.64.

Infrared Spectrum (KCl); 1655 cm$^{-1}$ (amide carbonyl).

N-[4-(7-β-Galactosylcoumarin-3-carboxamido)butyl]aminocarbonyl-5H-dibenz[b,f]azepine (14).

A mixture of 24 g of potassium hydroxide, 80 ml of water, 240 ml of methanol, and 20 g (0.035 mol) of ethyl 7-β-galactosylcoumarin-3-carboxylate [Burd et al, *Clin. Chem* 23:1402(1977)] was stirred at 50° C. for 15 hours. When cool, the methanol was removed under reduced pressure. The concentrated aqueous solution was acidified to pH 2.0 with concentrated hydrochloric acid. The white precipitate was collected, washed with cold water, and recrystallized from hot water. The crystals were collected, washed with acetone, and dried at 80° C. for 1 hour. This gave 12 g (54% yield) of 7-β-galactosylcoumarin-3-carboxylic acid as white crystals, mp 250°–255° C.

A mixture of 1.02 g (5 mmol) of dicyclohexylcarbodiimide, 575 mg (5 mmol) of N-hydroxysuccinimide, and 50 ml of dry dimethylformamide (DMF) was stirred at room temperature under argon for 30 minutes. The clear, colorless solution was cooled to −5° and 1.835 g (5 mmol) of 7-β-galactosylcoumarin-3-carboxylic acid was added. The reaction was allowed to warm to room temperature and stirred for 2 hours. The mixture was then cooled in an ice bath and the precipitate of dicyclohexyl urea removed by filtration under argon. The filtrate, now containing the N-hydroxysuccinimide ester (13), was combined with 1.54 g (5 mmol) of N-(4-aminobutyl)aminocarbonyl-5H-dibenz[b,f]azepine (12) dissolved in 5 ml of DMF. The reaction was stirred overnight at room temperature. The solvent was removed at 50° C./12 mm on the rotary evaporator and the residue triturated with dilute aqueous sodium bicarbonate solution. The insoluble material was chromatographed on 100 g of silica gel (E. Merck Co., Darmstadt, West Germany) eluting with a gradient of 2 L of ethyl acetate to 2 L of ethanol and 20 ml fractions were collected. Fractions 190 to 250 were combined, evaporated, and the residue recrystallized twice from ethanol. This gave 1.0 g (30% yield) of the labeled conjugate (14) as a white powder, mp 150°–160° C. (decomposed).

Analysis: Calculated for $C_{35}H_{35}N_3O_{10}$: C, 63.95; H, 5.35; N, 6.39. Found: C, 63.55; H, 5.77; N, 6.14.

Mass Spectrum (field desorption): m/e 658, [P+1].

Optical Rotation: $[\alpha]_D = -46.84°$ (c 1.0, MeOH)

The above-described synthesis of the β-galactosyl-coumarin-carbamazepine conjugate (14), n=4, can be modified to yield labeled conjugates wherein n=2 through 6 by replacing the starting material 1,4-diaminobutane with the appropriate α,ω-diaminoalkane as follows:

| n | α,ω-diaminoalkane |
|---|---|
| 2 | ethylenediamine |
| 3 | 1,3-diaminopropane |
| 5 | 1,5-diaminopentane |
| 6 | 1,6-diaminohexane |

B. Assay Reagents

1. Antiserum—Antiserum was obtained by immunization of rabbits with a carbamazepine-bovine serum albumin immunogen conjugate.

2. Enzyme and Buffer—Same as those described in Parts B-2 and B-3 in Example 9.

3. Carbamazepine standards—EMIT ® Antiepileptic Drug Calibrators (Syva Co., Palo Alto, CA) were prepared as described by the manufacturer.

4. Fluorogenic Carbamazepine Reagent—A solution was prepared in 5 mM formate—0.1% azide buffer, pH 3.5, which contained 0.016 $A_{343}$ units of β-galactosyl-umbelliferone-carbamazepine (Part A).

C. Assay Procedure and Results

Figure 13:
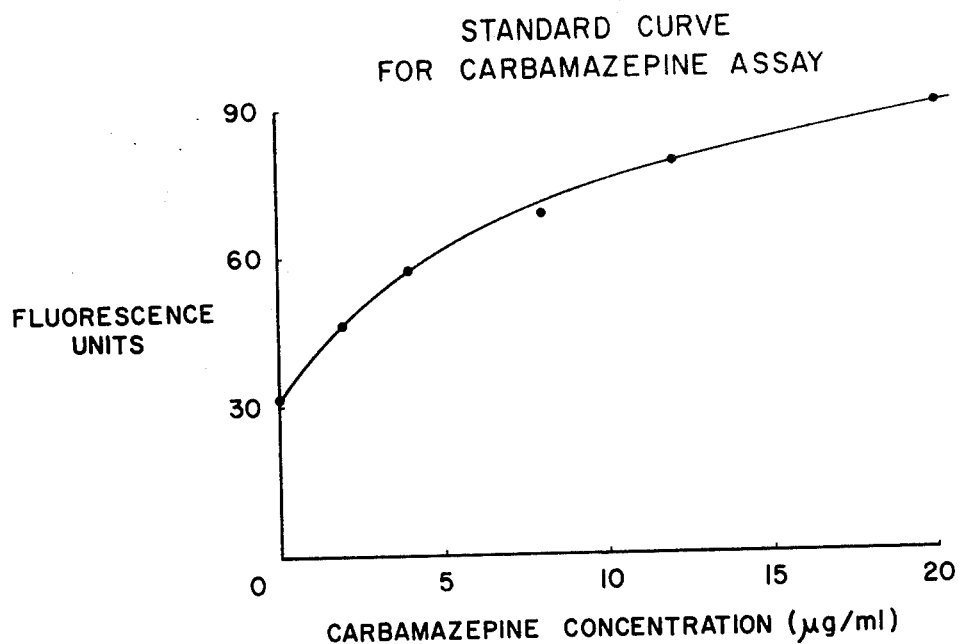

The procedure was the same as in Example 9 using carbamazepine standards and Fluorogenic Carbamazepine Reagent in place of the phenobarbital reagents. A standard curve generated for the assay of carbamazepine according to this procedure is depicted in FIG. 13 of the drawings.

EXAMPLE 12

Primidone Assay

Primidone [5-ethyl-5-phenylhexahydropyrimidine-4,6-dione, cf. The Merck Index, 9th ed., p. 1003(1976)], sold under various trademarks including Mysoline, is an anti-convulsant drug useful in the management of epilepsy. The therapeutic range of serum concentration in almost all patients lies between 5 and 10 μg/ml whereas toxicity almost invariably appears at blood levels over 15 μg/ml.

A. Preparation of glycone-dye-drug conjugate

The β-galactosyl-umbelliferone labeled primidone conjugates are prepared according to the reaction scheme shown in Table E in the drawings. This synthetic route is exemplified by the following method of preparing 5-[4-(7-β-galactosylcoumarin-3-carboxamido)butyl]-5-phenyl-2-desoxybarbituric acid (20), n=4.

Diethyl (3-Cyanopropyl)phenylmalonate (15)

A 50% mineral oil dispersion containing 16.8 g (0.7 mol) of sodium hydride was placed in a 3-liter, three-necked, round-bottom flask and washed free of oil with 500 ml of dry hexane. To this was added 1.2 liters of dry dimethylformamide (DMF) and 165.4 g (0.7 mol) of diethyl phenylmalonate (Aldrich Chemical Co., Milwaukee, WI). After hydrogen ceased to be evolved (3.5 hours), 104.2 g (0.7 mol) of 4-bromobutyronitrile (Aldrich Chemical Co.) was added, and the reaction heated at 65° C. overnight. The solvent was removed under reduced pressure, and the residue suspended in 1 liter of ethyl acetate. It was filtered, the filtrate reevaporated, and the residue evaporatively distilled at 170° C./0.1 mm to give 168 g (79% yield) of the diester (15) as a yellow liquid.

Analysis:

Infrared Spectrum (CDCl$_3$): 2245 cm$^{-1}$ (CN); 1730 cm$^{-1}$ (ester carbonyl).

NMR Spectrum (CDCl$_3$): δ1.3 (6H, t, J=8 Hz); δ7.3 (5H, s).

5-(3-Cyanopropyl)-5-phenyl-2-thiobarbituric Acid (16)

A solution of 11.5 g (0.5 g-atm) of sodium and 47.6 g (0.625 mol) of thiourea in 320 ml of absolute ethanol was stirred at reflux under an argon atmosphere. Over the next 30 minutes, 75.9 g (0.25 mol) of diethyl (3-cyanopropyl)phenylmalonate (15) was added dropwise. Heating was continued for 18 hours. When cool, the solvent was removed under reduced pressure, and the residue partitioned between 500 ml of water and 500 ml of ethyl acetate. The aqueous phase was separated, washed with ether, and acidified to pH 1 with concentrated hydrochloric acid. This aqueous mixture was allowed to evaporate to dryness to give a semicrystalline mass. It was digested with 350 ml of boiling chloroform, filtered, and cooled to give 20 g of a light tan solid, mp 130°–145° C. Recrystallization from ethanol gave 8 g (11% yield) of the cyano-thiobarbituric acid (16), as white crystals, mp 199° C.

Analysis: Calculated for $C_{14}H_{13}N_3O_2S$: C, 58.52; H, 4.56; N, 14.62. Found: C, 58.59; H, 4.39; N, 14.27.

Mass Spectrum (70 e.v.): m/e 287 [P+]; m/e 240 [PH+ minus CH$_2$CH$_2$CH$_2$CN].

5-(3-Cyanopropyl)-5-phenyl-2-desoxybarbituric Acid (17) and 5-(4-Aminobutyl)-5-phenyl-2-desoxybarbituric Acid (18)

A mixture of 8 g (0.029 mol) of 5-(3-cyanopropyl)-5-phenyl-2-thiobarbituric acid (16), 50 ml of an isopropanol slurry of freshly prepared W-5 raney nickel (R. L. Augustine, *Catalytic Hydrogenation*, Marcel Dekker, Inc., New York, 1965, page 27) and 300 ml of ethanol was stirred at reflux under a hydrogen atmosphere for 4 hours. It was filtered while hot and the filtrate cooled in an ice bath. The catalyst was washed with 200 ml of hot ethanol and then combined with the filtrate. When concentrated to a 50 ml volume, a yellow precipitate formed that amounted to 4.1 g when dry. This was chromatographed on 200 g of silica gel 60 (E. Merck Co., Darmstadt, West Germany). The column was eluted with 9:1 (v:v) toluene: methanol and 20 ml fractions were collected. Fractions 70 to 200 were combined, evaporated, and the residue twice recrystallized from ethanol to give 1.8 g (24% yield) of the cyanodesoxybarbituric acid (17) as fine white crystals, mp 253°–254° C.

Analysis: Calculated for $C_{14}H_{15}N_3O_2$: C, 65.35; H, 5.88; N, 16.33. Found: C, 65.09; H, 5.56; N, 15.71.

NMR Spectrum ($d_6$-DMSO): $\delta 4.0$ (m, 2H); $\delta 7.4$ (s, 5H).

The ethanol filtrate from the original crystallization was evaporated to give a glassy solid that was chromatographed on 250 g of silica gel using a solvent prepared by equilibrating equal volumes of chloroform, methanol, and concentrated ammonium hydroxide. The lower phase of this mixture was used to elute the column, and 15 ml fractions were collected. Fractions 66 to 100 were combined, evaporated, and the crystalline residue slurried in 2-propanol, filtered, and dried. This gave 180 mg (2% yield) of white crystals of the aminodesoxybarbituric acid (18), mp 242°–244° C.

Analysis:

NMR Spectrum ($d_4$—$CH_3OH$): $\delta 3.0$ (2H, t, J=8 Hz); $\delta 4.3$ (2H, m); $\delta 7.3$ (s, 5H).

Mass Spectrum (70 e.v.): m/e 261 [P+]; 218 [P+ minus $CH_2=CHNH_2$].

5-[4-(7-β-Galactosylcoumarin-3-carboxamido)butyl]-5-phenyl-2-desoxybarbituric Acid (20).

A mixture of 24 g of potassium hydroxide, 80 ml of water, 240 ml of methanol, and 20 g (0.035 mol) of ethyl 7-β-galactosylcoumarin-3-carboxylate [Burd et al, *Clin. chem.* 23, 1402 (1977)] was stirred at 50° C. for 15 hours. When cool, the methanol was removed under reduced pressure. The concentrated aqueous solution was acidified to pH 2 with concentrated hydrochloric acid. The precipitate was collected, washed with cold water, and recrystallized from hot water. The crystals were collected, washed with acetone, and dried at 80° C. for 1 hr. This gave 12 g (54% yield) of 7-β-galactosylcoumarin-3-carboxylic acid as white crystals, mp 250°–255° C.

A mixture of 210 mg (0.57 mmol) of 7-β-galactosylcoumarin-3-carboxylic acid and 5.7 ml of a 0.1 M solution of triethylamine in dry DMF was cooled to −10° C. white stirring under argon. To this was added 78 mg (0.57 mmol) of isobutyl chloroformate. After 15 minutes at −10° C., the reaction was allowed to warm to 0° C. for an additional 15 minutes. To this solution, now containing the mixed anhydride (19), was added 150 mg (0.57 mmol) of 5-(4-aminobutyl)-5-phenyl-2-desoxybarbituric acid (18) and another 5.7 ml of 0.1 M triethylamine-DMF solution. The reaction was stirred at 0° C. for 15 minutes, then allowed to come to room temperature overnight.

Two grams of silica gel 60 was added to the reaction mixture and the solvent evaporated under high vacuum. The impregnated silica gel was placed atop a column of 50 g of silica gel made up in ethyl acetate. The column was eluted with a gradient of 1 liter of ethyl acetate to 1 liter of ethanol, and 10 ml fractions were collected. Fractions 120 to 160 were combined and evaporated to give a white solid. Recrystallization from methanol gave 180 mg (51% yield) of the labeled conjugate (20) as a white powder, mp 181°–183° C.

Analysis: Calculated for $C_{30}H_{33}N_3O_{11}$: C, 58.91; H, 5.44; N, 6.89. Found: C, 55.86; H, 5.28; N, 6.37.

Mass Spectrum (Field Desorption): m/e 612 [PH+].

Optical Rotation: $[\alpha]_D = -48.38°$ (c 1.0, $CH_3OH$).

The above described synthesis of the β-galactosylcoumarin-primidone conjugate (20), n=4, can be modified to yield labeled conjugates wherein n=2 through 6 by replacing the starting material 4-bromobutyronitrile with the appropriate ω-bromoalkyl nitrile as follows:

| n | ω-bromoalkyl nitrile |
|---|---|
| 2 | 2-bromoacetonitrile |
| 3 | 3-bromopropionitrile |
| 5 | 5-bromovaleronitrile |
| 6 | 6-bromocapronitrile |

B. Assay Reagents

1. Antiserum—Antiserum was obtained by immunization of rabbits with a primidone-bovine serum albumin immunogen conjugate.
2. Enzyme and Buffer—Same as those described in Parts B-2 and B-3 in Example 9.
3. Primidone standards—Prepared from dried purified powder purchased from USP-NF Reference Standards.
4. Fluorogenic Primidone Reagent—A solution was prepared in 5 mM formate—0.1% azide buffer, pH 3.5, which contained 0.017 $A_{343}$ units of β-galactosyl-umbelliferone-primidone (Part A).

C. Assay Procedure and Results

Figure 14:
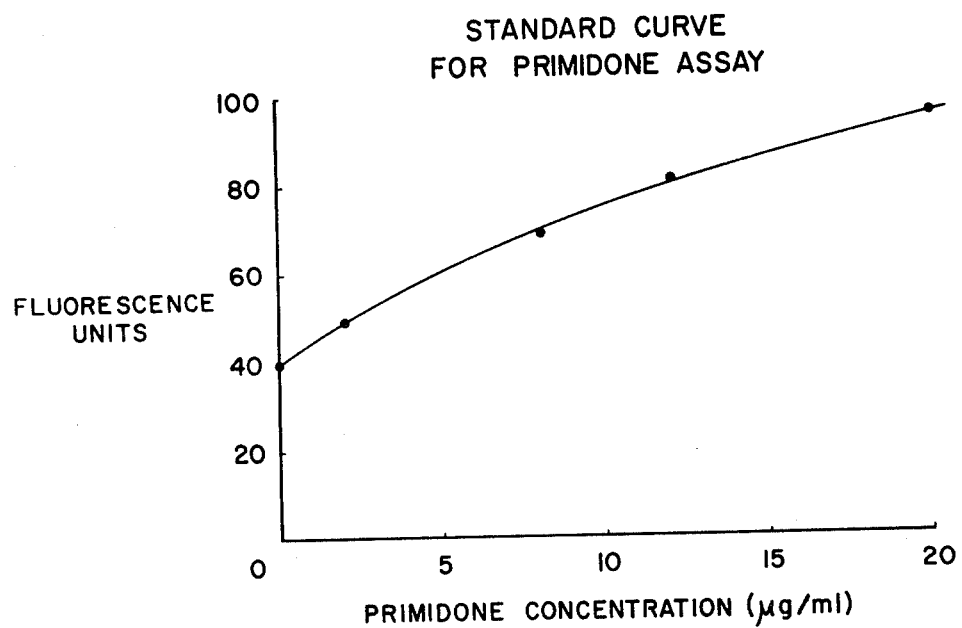

The procedure was the same as in Example 9 using primidone standards and Fluorogenic Primidone Reagent in place of the phenobarbital reagents. A standard curve generated for the assay of primidone according to this procedure is depicted in FIG. 14 of the drawings.

EXAMPLE 13

Immunoglobulin Assays

A. Preparation of glycone-dye-immunoglobulin conjugate

The β-galactosyl-umbelliferone labeled IgG conjugates are prepared according to the reaction scheme shown in Table F of the drawings. This synthetic route is exemplified by the following method of preparing labeled conjugate (22) wherein n=6, m=4 and p is on the average between 5 and 8.

N-(6-Aminohexyl)-7-β-galactosylcoumarin-3-carboxamide (21)

1,6-Hexanediamine (1.76 g, 15 mmoles) was dissolved in 20 ml of distilled water and the pH was adjusted to 9 with concentrated hydrochloric acid. 7-β-galactosylcoumarin-3-carboxylic acid (1.83 g, 5 mmoles) [Burd et al, *Clin. Chem.* 23:1402(1977)] was dissolved in the hexanediamine solution and the pH was further adjusted to 5±0.5. This solution was cooled to 4° C. in an ice bath. 1-Ethyl-3-(3-dimethylaminopropyl)carbodiimide (1.16 g, 6.15 mmoles) [Pierce Chemical Co., Rockford, IL] was added to the cooled solution and the pH was maintained at 5±0.5 manually. The reaction was allowed to proceed at 4° C. for two hours and then two more hours at room temperature. At the end of four hours, 80 ml water and 0.6 g (3.2 mmoles) 1-ethyl-3-(3-dimethylaminopropyl)carbodiimide were added to the reaction solution and the pH was maintained at 5. The solution was stirred continuously overnight at room temperature. Then it was diluted to 6 L with distilled water and applied onto a column (5×40 cm) of CM-Sepharose CL in the ammonium form [Pharmacia Fine Chemicals, Piscataway, NJ]. The column was washed successively with 3 L distilled water, 1 L of 1 mM ammonium bicarbonate and 2 L of 2 mM ammonium bicarbonate. The chromatogram was developed with a linear gradient generated with 4 L of 2 mM and 4 L of 300 mM ammonium bicarbonate and 10 ml fractions were collected. The absorbance of the eluate was monitored at 280 nm and selected fractions were examined by thin layer chromatography on silica gel 60 plates using a 0.5 M triethylammonium bicarbonate; pH 7.8: ethanol (3:7) solvent. The fractions eluted between 70 to 90 mM ammonium bicarbonate showed several fluorescent spots when viewed under long wavelength UV light and one spot, $R_f = 0.24$, gave a positive reaction with ninhydrin. These fractions were pooled and evaporated to dryness. The residue was dissolved in water and evaporated to dryness several times to remove the residual ammonium bicarbonate. The yield was less than 10%.

β-Galactosyl-umbelliferone labeled IgG (22)

To 8.5 mg (18 μmoles) of the above product in 2 ml of distilled water was added 10 mg (40 μmoles) dimethyladipimidate dihydrochloride [Pierce Chemical Co., Rockford, IL] and 40 μl triethylamine. The solution was stirred at room temperature for ten minutes and then 40 mg (0.26 μmole) human IgG [Miles Laboratories, Inc., Elkhart, IN] in 1 ml of 0.1 M sodium pyrophosphate buffer, pH 8.5, was addded. The solution was stirred at room temperature for two additional hours, after which the solution was applied onto a column (3×50 cm) of Sephadex G-25 coarse, equilibrated with 0.1 M sodium phosphate pH 7.0. Fractions of 7 ml were collected. They were monitored at 280 and 340 nm and those containing IgG were pooled and dialyzed at 4° C. successively against 6 L of 0.1 M sodium phosphate, pH 7.0; 6 L of 0.1 M sodium phosphate, pH 7.0, containing 1 M sodium chloride; and 6 L of 0.1 M sodium phosphate, pH 7.0, for 18 hours each.

The above described synthesis of the β-galactosyl-umbelliferone-IgG conjugate (22), n=6, m=4, can be modified to yield labeled conjugates wherein n=2-8 and m=1-10 by replacing the starting materials 1,6-hexanediamine and dimethyl adipimidate, respectively, with the appropriate α,ω-alkyldiamine and diemthyl alkyldiimidate as follows:

| n | α,ωalkyldiamine |
|---|---|
| 2 | ethylenediamine |
| 3 | 1,3-propanediamine |
| 4 | 1,4-butanediamine |
| 5 | 1,5-pentanediamine |
| 7 | 1,7-heptanediamine |
| 8 | 1,8-octanediamine |

| m | dimethyl alkyldiimidate |
|---|---|
| 1 | dimethyl malonimidate |
| 2 | dimethyl succinimidate |
| 3 | dimethyl glutarimidate |
| 5 | dimethyl pimelimidate |
| 6 | dimethyl octanediimidate |
| 7 | dimethyl nonanediimidate |
| 8 | dimethyl decanediimidate |
| 9 | dimethyl undecanediimidate |
| 10 | dimethyl dodecanediimidate |

B. Assay Reagents

1. Antiserum—Rabbit anti-human IgG obtained from Calbiochem, La Jolla, CA.
2. Enzyme and Buffer—Same as those described in Parts B-2 and B-3 in Example 9.
3. IgG standards—Pooled sera diluted 100-fold with the buffer.
4. Fluorogenic IgG Reagent—From Part A.

C. Assay Procedure and Results

To a plastic disposable cuvette was added sequentially 3.1 ml of the buffer containing 0.28 nmole (89 nM) of the Fluorogenic IgG Reagent, 0.1 ml of a selected standard, and 0.1 ml of the antiserum diluted 10-fold with the buffer (sufficient to decrease the enzyme reaction to about 10% of that observed in the absence of antiserum). The curvette was gently inverted for mixing and 0.1 ml of the enzyme solution containing 0.005 units of β-galactosidase was added and mixed by inversion. The solution was incubated at room temperature for 30 minutes and the fluorescence intensity measured with an Aminco-Bowman spectrofluorometer. Excitation and emission wavelengths were set at 400 and 450 nm, respectively, and all measurements were conducted at 25° C.

Figure 15:
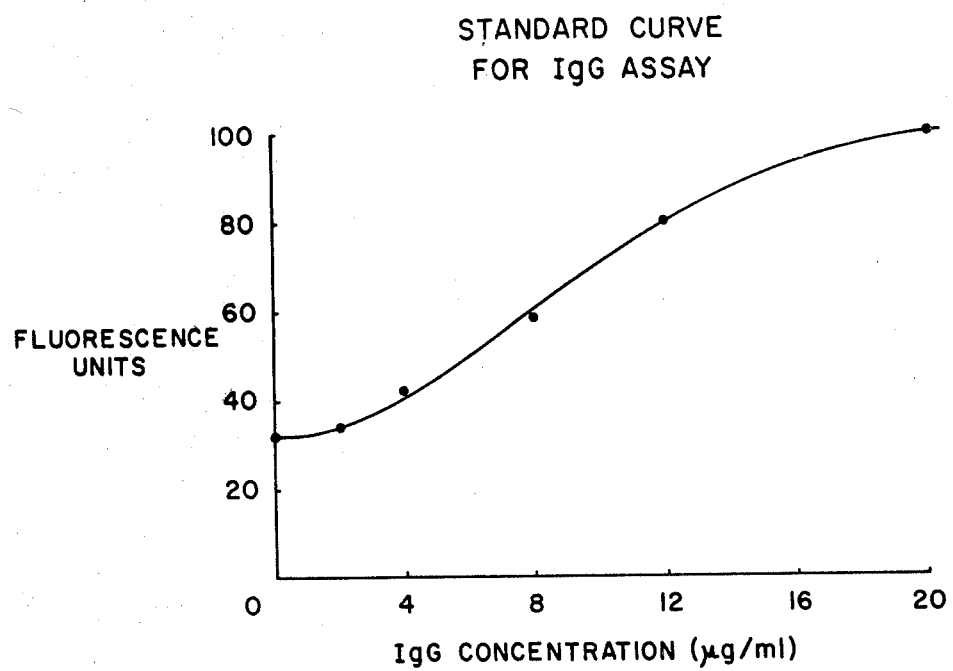

A standard curve generated for the assay of IgG according to this procedure is depicted in FIG. 15 of the drawings. The experiments were repeated for assaying IgM and IgA. Labeled conjugates were prepared according to the synthetic method of Part A. Results were similar to those for IgG.

What is claimed is:

1. A β-galactosyl-umbelliferone-labeled theophylline conjugate of the formula:

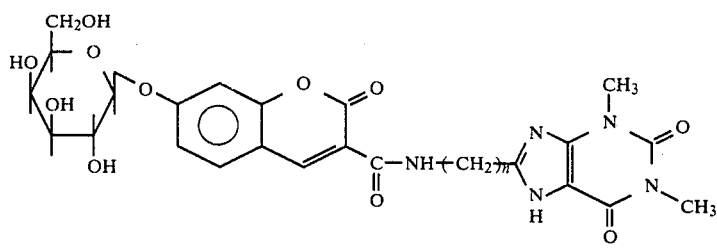

wherein n=2-6.

2. The conjugate of claim 1 wherein n=3.

3. A β-galactosyl-umbelliferone-labeled phenobarbital conjugate of the formula:

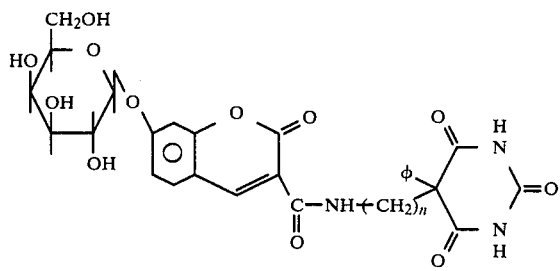

wherein φ is phenyl and n=2-6.

4. The conjugate of claim 3 wherein n=4.

5. A β-galactosyl-umbelliferone-labeled carbamazepine conjugate of the formula:

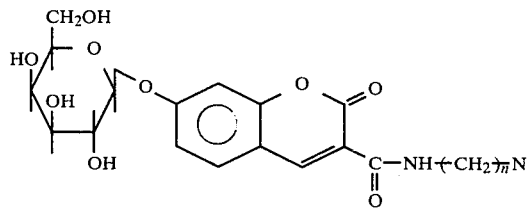

wherein n=2-6.

6. The conjugate of claim 5 wherein n=4.

7. A β-galactosyl-umbelliferone-labeled primidone conjugate of the formula:

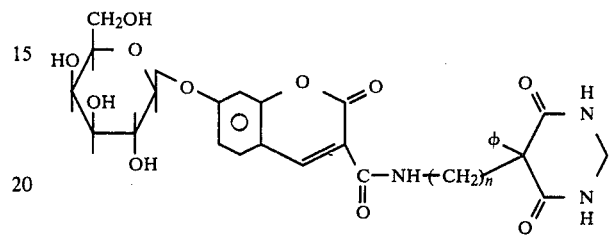

wherein φ is phenyl and n=2-6.

8. The conjugate of claim 7 wherein n=4.

9. A β-galactosyl-umbelliferone-labeled hapten conjugate of the formula:

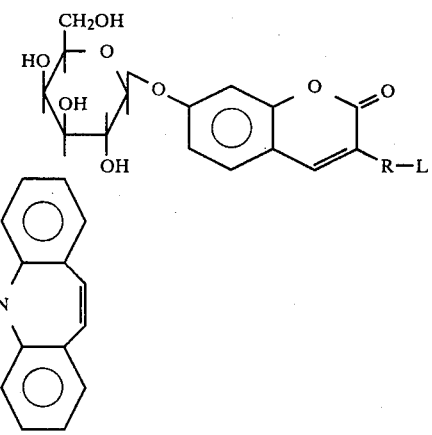

wherein R is a linking group and L is a hapten of molecular weight between 100 and 1000.

10. The conjugate of claim 9 wherein said linking group is a chain containing between 1 to 10 carbon atoms and 0 to 5 heteroatoms selected from nitrogen, oxygen and sulfur.

11. The conjugate of claim 9 wherein said hapten is selected from the group consisting of, diphenylhydantoin, phenobarbital, primidone, carbamazepine, ethosuximide, sodium valproate, theophylline, quinidine, procainamide, thyroxine, liothyronine, estriol, morphine, the barbiturates, the amphetamines, librium and valium.

* * * * *